US011952613B2

(12) United States Patent
Gray

(10) Patent No.: US 11,952,613 B2
(45) Date of Patent: Apr. 9, 2024

(54) METHODS AND REAGENTS FOR ENHANCED NEXT GENERATION SEQUENCING LIBRARY CONVERSION AND INCORPORATION OF MOLECULAR BARCODES INTO TARGETED AND RANDOM NUCLEIC ACID SEQUENCES

(71) Applicant: Red Genomics, Inc., Carlsbad, CA (US)

(72) Inventor: Phillip N. Gray, Carlsbad, CA (US)

(73) Assignee: Phillip N. Gray, Carlsbad, CA (US)

( * ) Notice: Subject to any disclaimer, the term of this patent is extended or adjusted under 35 U.S.C. 154(b) by 885 days.

(21) Appl. No.: 16/816,199

(22) Filed: Mar. 11, 2020

(65) Prior Publication Data
US 2021/0017572 A1 Jan. 21, 2021

Related U.S. Application Data

(60) Provisional application No. 62/958,221, filed on Jan. 7, 2020, provisional application No. 62/823,519, filed on Mar. 25, 2019, provisional application No. 62/816,231, filed on Mar. 11, 2019.

(51) Int. Cl.
*C12Q 1/6806* (2018.01)
*C12N 15/10* (2006.01)

(52) U.S. Cl.
CPC ....... *C12Q 1/6806* (2013.01); *C12N 15/1037* (2013.01); *C12N 15/1068* (2013.01)

(58) Field of Classification Search
None
See application file for complete search history.

(56) References Cited

U.S. PATENT DOCUMENTS

| 6,916,632 | B2 | 7/2005 | Chesnut et al. |
| 2003/0022179 | A1 | 1/2003 | Chesnut et al. |
| 2015/0024950 | A1* | 1/2015 | Bielas et al. ............ C40B 50/06 506/17 |
| 2015/0044687 | A1* | 2/2015 | Schmitt et al. ...... C12Q 1/6806 435/6.12 |
| 2015/0197787 | A1 | 7/2015 | Welder et al. |

FOREIGN PATENT DOCUMENTS

WO 2009/017673 A2 2/2009

OTHER PUBLICATIONS

Okou et al., Microarray-based genomic selection for high-throughput resequencing, Nat. Methods, 2007, 907-909, 4(11).
Patel et al., Identification of essential genes for cancer immunotherapy, Nature, 2017, 537-542, 548(7669).
(Continued)

*Primary Examiner* — Kaijiang Zhang

(57) ABSTRACT

Novel engineered compositions, reagents, and methods are described that facilitate NGS analysis of both random and specific nucleic acid sequences in a sample by providing high efficiency target enrichment and improved error suppression. Specifically, the design and use of engineered NGS dual adapter molecules with homology regions (HRs) targeted at the 5' and 3' regions of a double-stranded DNA target, unique molecule identifiers (UMIs), and NGS adapters allows target libraries to be created for subsequent NGS analysis.

3 Claims, 9 Drawing Sheets

Specification includes a Sequence Listing.

(56) References Cited

OTHER PUBLICATIONS

Potapov et al., Examining Sources of Error in PCR by Single-Molecule Sequencing, 2017, PLoS ONE, e0169774, 12(1) (19 pages).
Pritchard et al., Validation and implementation of targeted capture and sequencing for the detection of actionable mutation, copy number variation, and gene rearrangement in clinical cancer specimens, J. Mol. Diagn., 2014, 56-67, 16(1).
Radding, Helical interactions in homologous pairing and strand exchange driven by RecA protein, J. Biol. Chem., 1991, 5355-5358, 266(9).
Rahner et al., Hereditary cancer syndromes, Dtsch. Arztebl. Int., 2008, 706-714, 105(41).
Rao et al., Stable three-stranded DNA made by RecA protein, Proc. Natl. Acad. Sci. USA, 1991, 2984-2988, 88(8).
Roche Sequencing, Avenio ctDNA Targeted Kits for NGS Liquid Biopsy, [retrieved on Mar. 20, 2020], Retrieved from the Internet:< URL: https://sequencing.roche.com/en-us/products-solutions/by-category/assays/ctdna-analysis-kits/ctdna-targeted-kits.html> (6 pages).
Rosati et al., Overview of methodologies for T-cell receptor repertoire analysis, BMC Biotechnol., 2017, 61, 17(1) (16 pages).
Schmitt et al., Detection of ultra-rare mutations by next-generation sequencing, Proc. Natl. Acad. Sci. USA, 2012, 14508-14513, 109(36).
Shembekar et al., Droplet-based microfluidics in drug discovery, transcriptomics and high-throughput molecular genetics, Lab Chip, 2016, 1314-1331, 16(8).
Shibata et al., Purification of recA protein from *Escherichia coli*, Methods Enzymol., 1983, 197-209, 100.
Shinohara et al., Cloning of human, mouse and fission yeast recombination genes homologous to RAD51 and recA, Nat. Genet., 239-243, 4(3).
Shu et al., Circulating Tumor DNA Mutation Profiling by Targeted Next Generation Sequencing Provides Guidance for Personalized Treatments in Multiple Cancer Types, Sci. Rep., 2017, 583, 7 (11 pages).
Shuman, Novel approach to molecular cloning and polynucleotide synthesis using vaccinia DNA topoisomerase, J. Biol. Chem., 1994, 32678-32684, 269(51).
Shuman, Recombination Mediated by Vaccinia Virus DNA Topoisomerase I in *Escherichia coli* is Sequence Specific, Proc. Natl. Acad. Sci. USA, 1991, 10104-10108 88(22).
Talerico et al., Effect of 5' Splice Site Mutations on Splicing of the Preceding Intron, Mol. Cell. Biol., 1990, 6299-6305, 10(12).
Tate et al., COSMIC: the Catalogue Of Somatic Mutations In Cancer, Nucleic Acids Res., 2019, D941-D947, 47(D1).
Tracy et al., In vitro selection of preferred DNA pairing sequences by the *Escherichia coli* RecA protein, Genes Dev. 1996, 1890-1903, 10(15).
Treangen et al., Repetitive DNA and next-generation sequencing: computational challenges and solutions, Nat. Rev. Genet., 2011, 36-46, 13(1).
Treangen et al., Erratum: Repetitive DNA and next-generation sequencing: computational challenges and solutions, Nat. Rev. Genet., 2012, 146, 13(2).
Van Dijk et al., The third revolution in sequencing technology, Trends Genet., 2018, 666-681, 34(9).
Wagle et al., High-throughput detection of actionable genomic alterations in clinical tumor samples by targeted, massively parallel sequencing, Cancer Discov. 2011, 82-93, 2(1).
Westdorp et al., Opportunities for immunotherapy in microsatellite instable colorectal cancer, Cancer Immunol. Immunother., 2016, 1249-1259, 65(10).
Wikipedia, Edit distance, [retrieved Mar. 28, 2020], Retrieved from the Internet:< URL: https://en.wikipedia.org/wiki/Edit_distance> (6 pages).
Wikipedia, Levenshtein distance, [retrieved Mar. 28, 2020], Retrieved from the Internet:< URL: https://en.wikipedia.org/wiki/Levenshtein_distance> (pages).

Yang et al., Antitumor Activity of BRAF Inhibitor Vemurafenib in Preclinical Models of BRAF-Mutant Colorectal Cancer, Cancer Res., 2012, 779-789, 72(3).
Yonesaki et al., T4 phage gene uvsX product catalyzes homologous DNA pairing, EMBO J., 1985, 3321-3327, 4(12).
Zhang et al., Seamless Ligation Cloning Extract (SLiCE) Cloning Method, Methods Mol. Biol., 2014, 235-244, 1116.
Zhumabayeva et al., RecA-Mediated Affinity Capture: A Method for Full-Length cDNA Cloning, BioTechniques, 1999, 834-845, 27(4).
Abkevich et al., Patterns of genomic loss of heterozygosity predict homologous recombination repair defects in epithelial ovarian cancer, Br. J. Cancer, 2012, 1776-1782, 107(10).
Albert et al., Direct selection of human genomic loci by microarray hybridization, Nat. Methods, 2007, 903-905, 4(11).
Allyse et al., Non-invasive prenatal testing: a review of international implementation and challenges, Int. J. Womens Health, 2015, 113, 7 (14 pages).
Angov et al., The recA gene from the thermophile Thermus aquaticus YT-1: cloning, expression, and characterization, J. Bacteriol., 1994, 1405-1412, 176(5).
Bacher et al., Development of a fluorescent multiplex assay for detection of MSI-high tumors, Dis. Markers, 2004, 237-250, 20(4-5).
Barnard et al., Pcr bias toward the wild-type k-ras and p53 sequences: Implications for pcr detection of mutations and cancer diagnosis, BioTechniques, 1998, 684-691, 25(4).
Carethers et al., EMAST is a Form of Microsatellite Instability That is Initiated by Inflammation and Modulates Colorectal Cancer Progression, Genes, 2015, 185-205, 6(2).
Chan et al., Development of Tumor Mutation Burden as an Immunotherapy Biomarker: Utility for the Oncology Clinic, Ann. Oncol., 2019, 44-56, 30(1).
Chaudhary et al., Analyzing Immunoglobulin Repertoires, Front. Immunol., 2018, 462, 9 (18 pages).
Chong et al., The Validation and Clinical Implementation of BRCAplus: A Comprehensive High-Risk Breast Cancer Diagnostic Assay, 2014, PLoS ONE, e97408, 9(5) (10 pages).
Costello et al., Discovery and characterization of artifactual mutations in deep coverage targeted capture sequencing data due to oxidative DNA damage during sample preparation, Nucleic Acid Research, 2013, e67, 41(6) (12 pages).
Coupland et al., Direct sequencing of small genomes on the Pacific Biosciences RS without library preparation, Biotechniques, 2012, 365-372, 53(6).
Fiala et al., Utility of circulating tumor DNA in cancer diagnostics with emphasis on early detection, BMC Medicine, 2018, 166, 16 (10 pages).
Fox et al., Accuracy of Next Generation Sequencing Platforms, Next Gener. Seq Appl., 2014, 1000106, 1 (9 pages).
Frampton et al., Development and validation of a clinical cancer genomic profiling test based on massively parallel DNA sequencing, Nat. Biotechnol., 2013, 1023-1031, 31(11).
Fu et al., Elimination of PCR duplicates in RNA-seq and small RNA-seq using unique molecular identifiers, BMC Genomics, 2018, 531, 19(1) (14 pages).
Gasior et al., Assembly of RecA-like recombinases: Distinct roles for mediator proteins in mitosis and meiosis, Proc. Natl. Acad. Sci. USA, 2001, 8411-8418, 98 (15).
Gibson et al., Chemical synthesis of the mouse mitochondrial genome, Nat. Methods, 2010, 901-903, 7(11).
Gibson et al., Enzymatic assembly of DNA molecules up to several hundred kilobases, Nat. Methods, 2009 343-345, 6(5).
Giornelli, Management of relapsed ovarian cancer: a review, Springerplus, 2016, 1197, 5(1) (11 pages).
Gray et al., Not All Next Generation Sequencing Diagnostics are Created Equal: Understanding the Nuances of Solid Tumor Assay Design for Somatic Mutation Detection, Cancers, 2015, 1313-1332, 7(3).
Hahn et al., Allele drop-out can occur in alleles differing by a single nucleotide and is not alleviated by preamplification or minor template increments, Genet. Test 1998, 351-355, 2(4).
Havel et al., The evolving landscape of biomarkers for checkpoint inhibitor immunotherapy, Nat. Rev. Cancer, 2019, 19, 133-150, 133(Suppl. 5).

(56) References Cited

OTHER PUBLICATIONS

Hodges et al., Genome-wide in situ exon capture for selective resequencing, Nat. Genet., 2007, 1522-1527, 39(12).

Holmes et al., Mechanistic signatures of HPV insertions in cervical carcinomas, NPJ Genom. Med., 2016, 1-16, 1.

Honigberg et al., Ability of RecA protein to promote a search for rare sequences in duplex DNA, Proc. Natl. Acad. Sci. USA, 1987, 9586-9590, 83(24).

Hsieh et al., The synapsis event in the homologous pairing of DNAs: RecA recognizes and pairs less than one helical repeat of DNA, Proc. Natl. Acad. Sci. USA, 1992, 6492-6496, 89(14).

Kamps et al., Next-Generation Sequencing in Oncology: Genetic Diagnosis, Risk Prediction and Cancer Classification, Int. J. Mol. Sci., 2017, 308,18(2) (57 pages).

Kato et al., Characterization of thermostable RecA protein and analysis of its interaction with single-stranded DNA, Eur. J. Biochem., 1999, 592-601, 259(3).

Kawashima et al., Functional domains of *Escherichia coli* recA protein deduced from the mutational sites in the gene, Molec. Gen. Genet., 1984, 288-292, 193(2).

Khozin et al., U.S. Food and Drug Administration approval summary: Erlotinib for the first-line treatment of metastatic non-small cell lung cancer with epidermal growth factor receptor exon 19 deletions or exon 21 (L858R) substitution mutations, Oncologist, 2014, 774-779, 19(7).

Kirkpatrick et al., RecA protein promotes rapid RNA-DNA hybridization in heterogeneous RNA mixtures, Nucleic Acids Res., 1992, 4347-4353, 20(16).

Kmiec et al., Homologous pairing of DNA molecules promoted by a protein from Ustilago, Cell, 1982, 367-374, 29(2).

Knight et al., Donor-specific Cell-free DNA as a Biomarker in Solid Organ Transplantation. A Systematic Review, Transplantation, 2019, 273-283, 103(2).

Kohlmann et al., In Adams et al. (Eds)., Lynch Syndrome, GeneReviews® [Internet], 2004 [Updated Apr. 12, 2018], 1-33, University of Washington, Seattle, WA.

Kohn et al., The HRD decision—which PARP inhibitor to use for whom and when, Clin. Cancer Res. 2017, 7155-7157, 23(23).

Kowalcyzkowski et al., Homologous Pairing and DNA Strand-Exchange Proteins, Annu. Rev. Biochem., 1994, 991-1043, 63(1).

Kowalcyzkowski, Biochemistry of Genetic Recombination: Energetics and Mechanism of DNA Strand Exchange, Annu. Rev. Biophys. Biophys. Chem., 1991, 539-575, 20(1).

Lanman et al., Analytical and Clinical Validation of a Digital Sequencing Panel for Quantitative, Highly Accurate Evaluation of Cell-Free Circulating Tumor DNA, PLoS ONE, 2015, e0140712, 10(10) (27 pages).

Lee et al., CRISPR-Cap: multiplexed double-stranded DNA enrichment based on the CRISPR system, Nucleic Acids Res., 2019, e1, 47(1) (13 pages).

Levine et al., Global Manufacturing of CAR-T Cell Therapy, Mol. Ther. Methods Clin. Dev., 2017, 92-101, 4.

Li et al., SLIC: a method for sequence- and ligation-independent cloning, Methods Mol. Biol., 2012, 51-59, 852.

Lovett et al., Purification of a RecA protein analogue from Bacillus subtilis, J. Biol. Chem., 1985, 3305-13, 260(6).

Madiraju et al., Properties of a mutant recA-encoded protein reveal a possible role for *Escherichia coli* recF-encoded protein in genetic recombination, Proc. Natl. Acad. Sci. USA, 1988, 6592-6596, 85(18).

Maher et al., Transcriptome Sequencing to Detect Gene Fusions in Cancer, Nature, 2009, 97-101, 458(7234).

Mamanova et al., Target-enrichment strategies for next-generation sequencing, Nat. Methods, 2010, 111-118, 7(2).

Mertens et al., The emerging complexity of gene fusions in cancer, Nat. Rev. Cancer, 2015, 371-381, 15(6).

Nachmanson et al., Targeted genome fragmentation with CRISPR/Cas9 enables fast and efficient enrichment of small genomic regions and ultra-accurate sequencing with low DNA input (CRISPR-DS), Genome Res., 2018, 1589-1599, 28(10).

New England Biolabs, NEBuilder® HiFi DNA Assembly Master Mix, [retrieved Mar. 20, 2020], Retrieved from the Internet:< URL: https://www.neb.com/products/e2621-nebuilder-hifi-dna-assembly-master-mix#Product%20Information> (14 pages).

Newman et al., Integrated digital error suppression for improved detection of circulating tumor DNA, Nat. Biotechnol., 2016, 547-555, 34(5).

* cited by examiner

Fig. 2A
Dual Adapter probe with one HR region to capture gene fusions

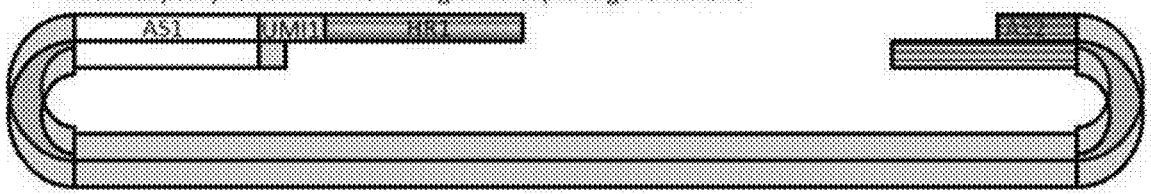

Fig. 2B
Probe HR1 region can hybridize to either mRNA or cDNA of a gene fusion. If capturing mRNA, reverse transcriptase primes off the HR region to make the reverse complement.

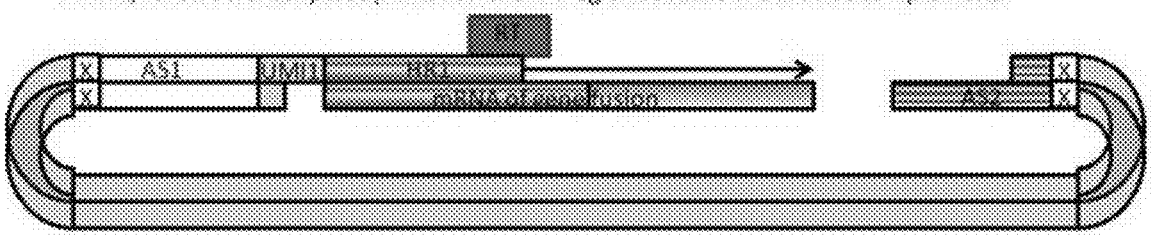

Fig. 2C
Probe HR1 region can hybridize to either mRNA or cDNA of a gene fusion. If capturing mRNA, reverse transcriptase primes off the HR region to make the reverse complement.

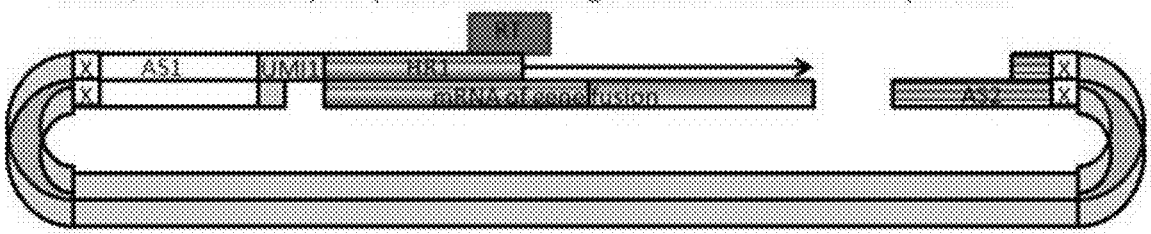

Fig. 2D
End Repair followed by blunt ligation.

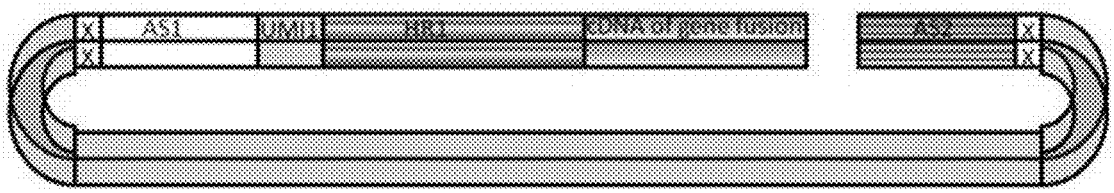

Fig. 2E
Dual Adapter Probe with captured sample gene fusion cDNA. Primers that bind to AS1 and AS2 are used to amplify the final NGS library that is ready for sequencing.

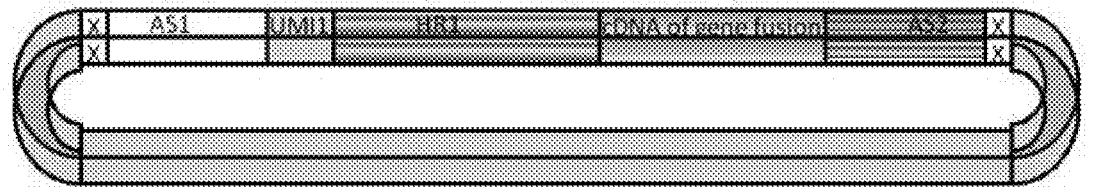

Fig. 4A

Topoisomerase (TOPO) Dual Adapter Molecule
Topoisomerase-Based UMI-Adapter Attachment paired with Recombinase-mediated Target Enrichment

TOPO = Topoisomerase enzyme      CCCTT = Topoisomerase attachment/binding sequence

Fig. 4B

Sample DNA fragment is covalently attached to the TOPO-Dual Adapter molecule

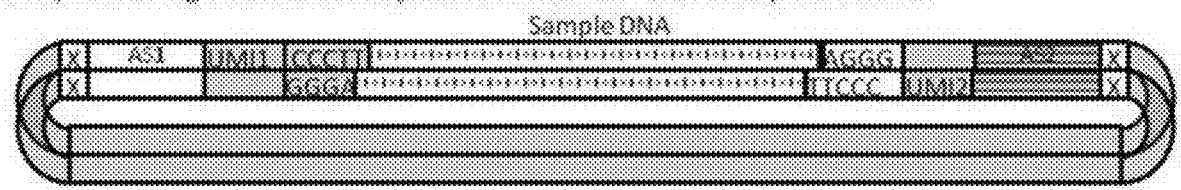

Fig. 4C

Circular dsDNA Dual Adapter molecule with sample DNA can be combined with nucleofilaments composed to biotinylated oligonucleotides and recombinase protein, such as RecA, for target enrichment.

RecA facilitates hybridization of oligonucleotides to complementary sample nucleic acid in the TOPO-Dual Adapter molecule

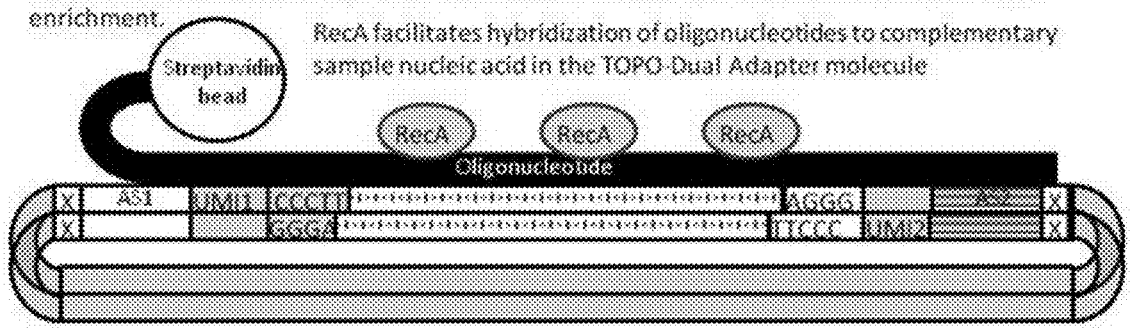

Fig. 4D

Sample DNA is eluted from probes. Primers that bind NAS sequences may be used to amplify the eluted DNA with either PCR or RCA, which can be loaded directly on an NGS system.

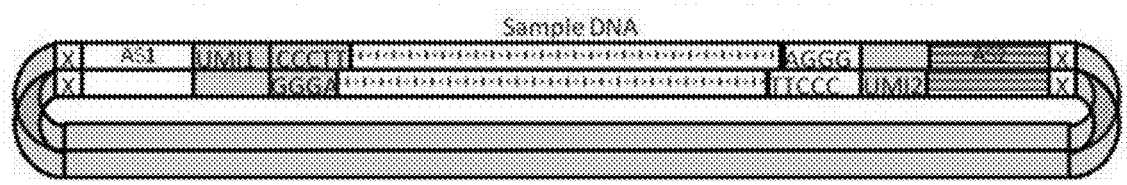

Fig. 5A
Rolling Circle Amplification (RCA) of Dual Adapter with sample DNA

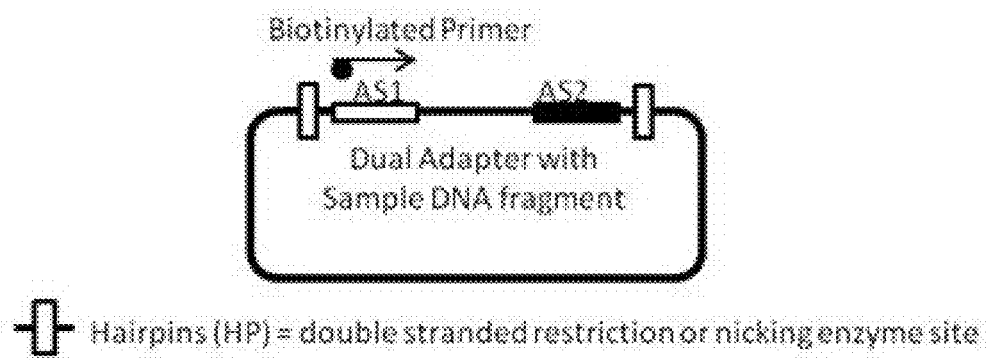

Hairpins (HP) = double stranded restriction or nicking enzyme site

AS1 and AS2 may be the full length P5 and P7 Illumina sequences that are required to attach to a flowcell and amplify

Fig. 5B
RCA generates biotinylated ssDNA concatemers:
AS1/UMI1/HR1 or TOPO/sample DNA/HR2 or TOPO/UMI2/AS2/HP/*/HP

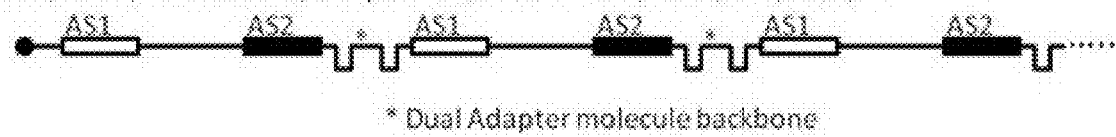

* Dual Adapter molecule backbone

Fig. 5C
Biotinylated ssDNA concatemers are isolated and purified using streptavidin beads

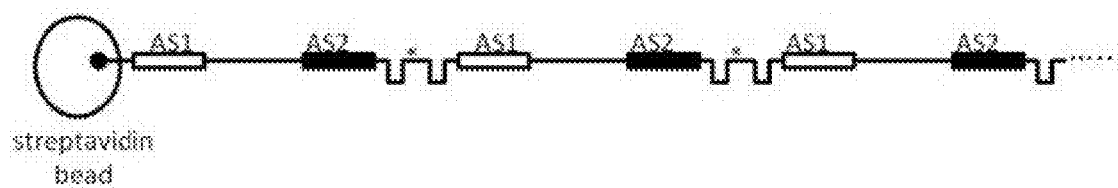

streptavidin bead

Fig. 5D
Purifed ssDNA concatemers are digested with the restriction (or nicking) enzyme corresponding to the sequence in hairpin. Digested ssDNA can be loaded directly on to sequencer

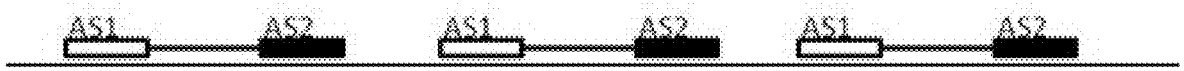

Fig. 6A
HR Adapter structure is similar to Dual Adapter probes except the HR1 and HR2 regions are on 2 separate Y-shaped molecules.

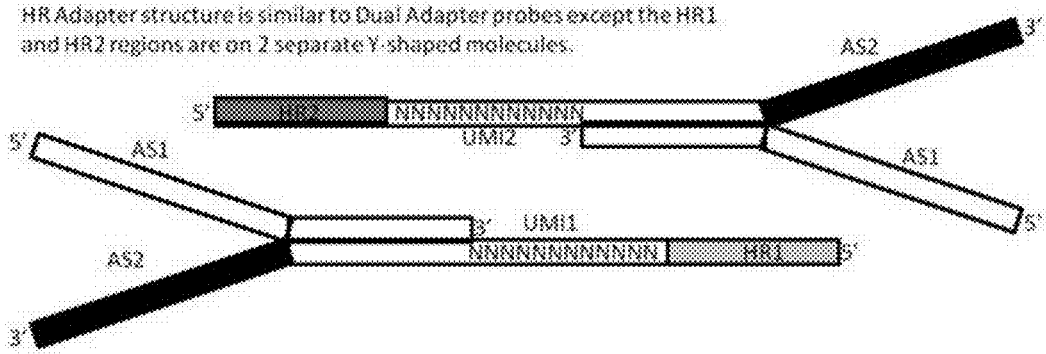

Fig. 6B
HR Adapters hybridize to complementary singled stranded regions in sample DNA that has been treated with an enzyme with exonuclease activity. DNA polymerase extends 3' ends of adapters and target sequence and Taq DNA Ligase seals the phosphate backbone

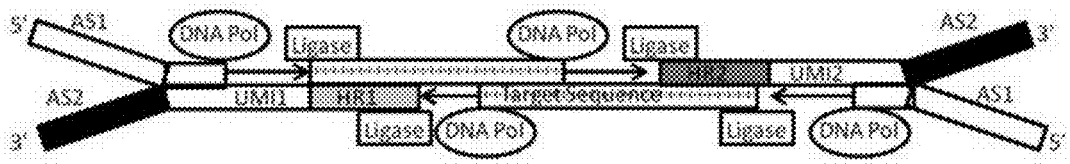

Fig. 6C
Final captured DNA with attached HR Adapters

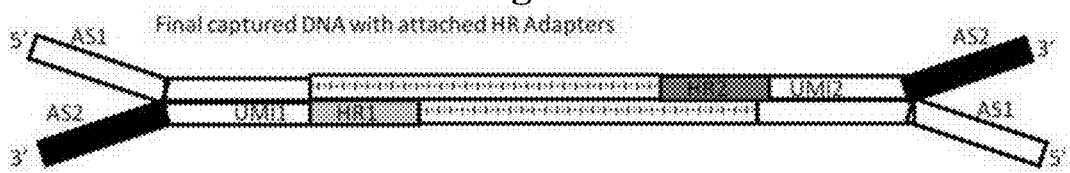

Fig. 6D
PCR products are created by using primers directed at the AS1 and AS2 sequences located in the HR Adapters. The PCR products are the final NGS library.

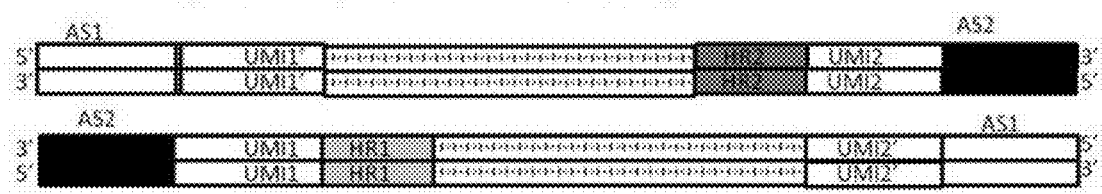

Fig. 7A

TOPO UMI Adapters consist of 4 oligonucleotides hybridized together with the UMI sequence single stranded.

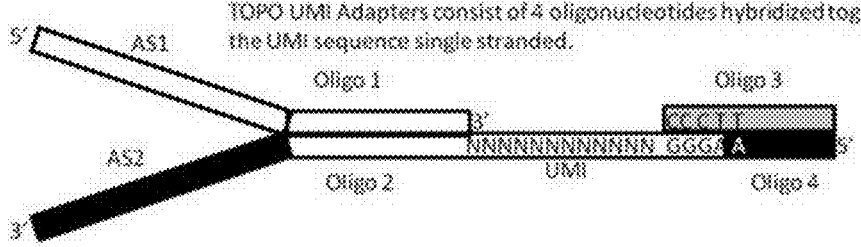

Fig. 7B

DNA polymerase extends 3' end of Oligo 1 to make the complement of the UMI sequence. Taq Ligase seals the backbone connecting Oligo 1 and Oligo 3.

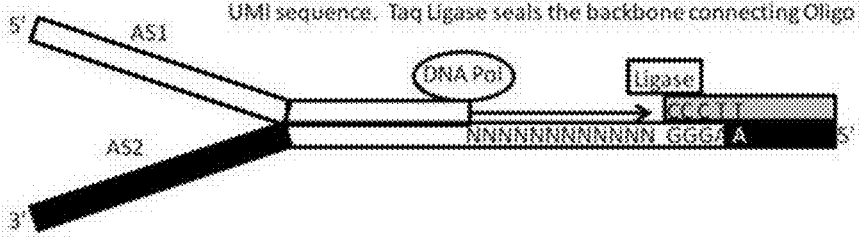

Fig. 7C

Topoisomerase binds the CCCTT sequence and covalently attaches to the second "T" and cleaves the phosphodiester bond just 3' to the CCCTT sequence.

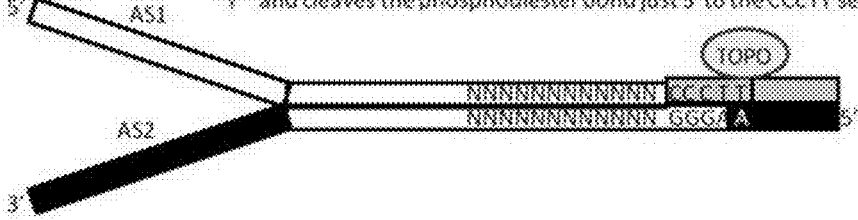

Fig. 7D

Upon Topoisomerase binding and phosphodiester bond cleavage, Oligo 4 and part of Oligo 3 dissociate, trapping Topoisomerase on the TOPO Adapter.

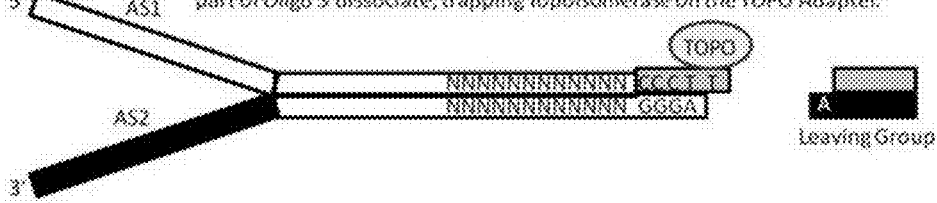

Fig. 7E

A-tailed sample DNA may hybridize to the overhanging T from the CCCTT sequence. Topoisomerase covalently links the adapter to the sample DNA and dissociates.

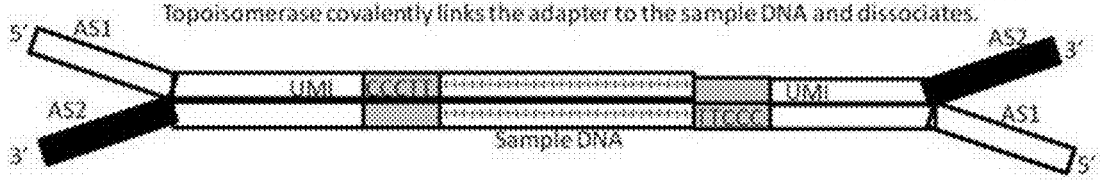

Fig. 8A
Capture and Adapt (CAAD) probes

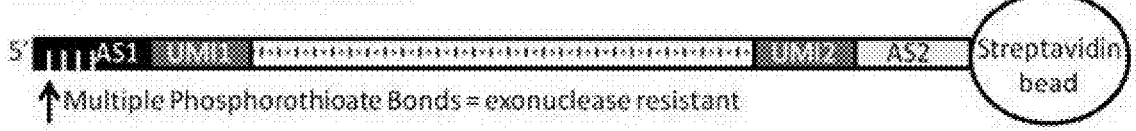

↑ Multiple Phosphorothioate Bonds = exonuclease resistant

Fig. 8B
Target DNA binds to CAAD probe

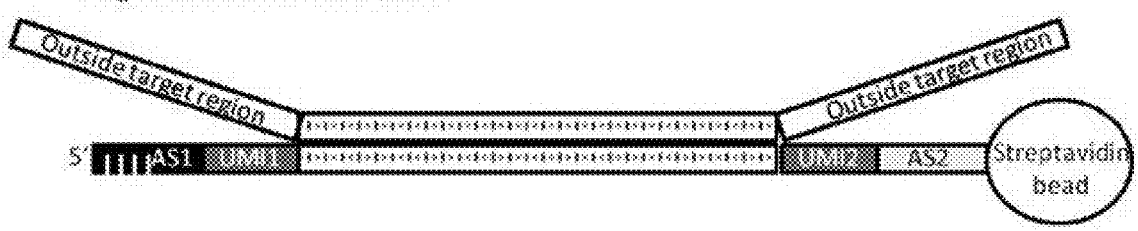

Fig. 8C
Mung Bean Nuclease (MBN) removes 5' and 3' single stranded overhangs. Probe is protected by phosphorothioate bonds at the 5' end and streptavidin bead at the 3' end.

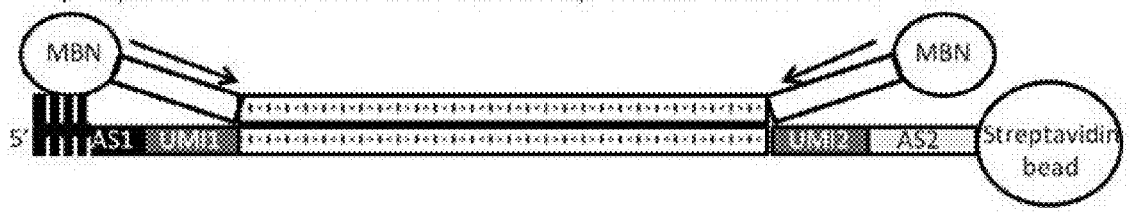

Fig. 8D
Residual single stranded regions are filled in by DNA Polymerase and Ligase seals the backbone.

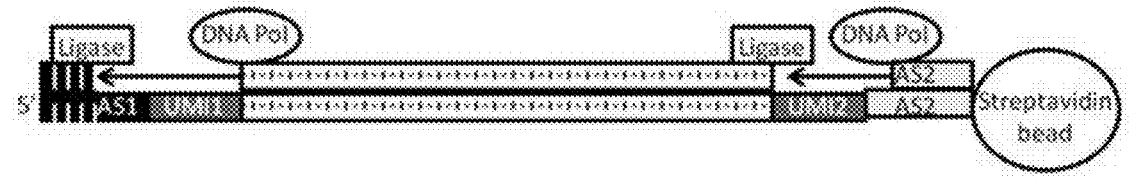

Fig. 8E
Final target sequence with UMIs and primer binding sites

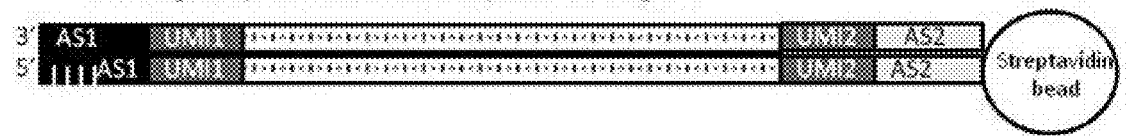

Fig. 8F
Elute Complementary DNA from CAAD probe, PCR and Sequence on NGS system

METHODS AND REAGENTS FOR ENHANCED NEXT GENERATION SEQUENCING LIBRARY CONVERSION AND INCORPORATION OF MOLECULAR BARCODES INTO TARGETED AND RANDOM NUCLEIC ACID SEQUENCES

RELATED APPLICATIONS

This application claims priority to U.S. provisional patent application No. 62/816,231, filed on Mar. 11, 2019, U.S. provisional patent application No. 62/823,519, filed on Mar. 25, 2019, and U.S. provisional patent application No. 62/958,221, filed on Jan. 7, 2020. All of the aforementioned priority applications are herein expressly incorporated by reference, each in its entirety, for any and all purposes.

BACKGROUND OF INVENTION

Next generation sequencing (NGS) based cancer diagnostic testing falls primarily into three categories: germline, somatic and liquid biopsy/ctDNA. Assay and bioinformatics analysis design, and data requirements vary dramatically across these sample types due to the level of sensitivity required for each. Germline DNA is the least challenging as samples are homogeneous and variants are at a high frequency, either in a homo or heterozygous state. Confident variant calling can be made at 40× coverage, which means each nucleotide analyzed has an average of 40 sequencing reads covering each base in the target sequence. Somatic/solid tumor samples are usually a heterogeneous mixture of cells derived from both tumor and normal tissue. Moreover, the tumor cells may consist of several subpopulations of mutant genotypes similar to a viral quasispecies. As a result, allele frequencies within the tumor may occur across a broad range, with mutations of interest present at low levels (i.e. 5%). As a result, tumor specimens require about 25-fold more sequence data (or 1000× coverage) than germline samples and an effective method to detect errors since mutations can occur at low frequencies. ctDNA is tumor-derived DNA that circulates in the blood at low frequency and is the most challenging specimen type. The levels of detectable ctDNA in the blood depend on cancer type and stage, with stage 4 cancer showing the highest levels. Due to the low frequency of ctDNA in blood, approximately 30,000-40,000× coverage is required for confident mutation detection. Moreover, the mutations in ctDNA are rare events and occur at the same frequency as errors introduced by sample processing (enzymatic errors, sample oxidation, etc.), so a method to distinguish true variants from artifacts is essential [1-4].

Current methods for isolating regions of DNA (i.e. exons in specific genes) for sequence analysis using next generation sequencing (NGS) technology are limited to either polymerase chain reaction (PCR) or probe-based target enrichment. PCR-based methods require the production of multiple primer pairs, each targeting a specific region. Due to the relatively small size of primer sequences, it is generally possible to design primers that do not amplify pseudogenes and can avoid most GC rich regions. Therefore, primer design strategies can generally achieve 100% coverage of a region of interest with minimal off-target sequence. Moreover, techniques that involve primary and secondary PCR allow targeted NGS libraries to be created fast and efficiently, only using enzymes and primers required for the PCR reactions. However, amplification-based target enrichment is susceptible to allele drop-out, which can result in false negatives. Allele drop-out occurs when a variant is located in a primer binding site and prevents primer hybridization, leading to failed amplification and allele bias [5-6]. The risk of allele drop-out can be reduced by a tiling primer design that results in multiple overlapping amplicons for each target. This strategy is sufficient for germline DNA samples, but may not completely prevent allele drop-out in somatic cancer samples (i.e. solid tumor and ctDNA) due to their heterogeneous nature. DNA isolated from a population of somatic cancer cells or ctDNA specimens will contain multiple acquired genotypes with varying allele frequencies. As these mutations can be present anywhere in the target region, allele drop-out may still occur if mutations are located in two adjacent primer binding sites.

Probe-based enrichment methods utilize long oligonucleotides complementary to a region of interest. Current probe-based platforms such as SureSelect from Agilent Technologies (Santa Clara, CA, USA), Lockdown Probes from Integrated DNA Technologies (Coralville, IA, USA) and SeqCap EZ from Roche-Nimblegen (Madison, WI, USA) use biotinylated oligonucleotide probes up to 120 nucleotides in length that are designed to capture a region of interest. Since the probes are much longer than typical PCR primers, variants in the probe binding site typically do not affect hybridization to the target region and thus allele drop-out is not an issue. This makes probe-based capture ideal for tumor and ctDNA samples where mutation burden may be high and rare variant detection is desired [7-13].

Probe-based library generation requires a multi-step preparation method that involves a pre- and post-enrichment PCR and requires extended incubation periods for efficient probe binding. Typically, the library preparation begins with DNA shearing, followed by the addition of repair enzymes to fill-in any single-stranded regions. The resulting blunt-ended double-stranded DNA (dsDNA) is treated with a polymerase to add a single "A" base to the end of each molecule. Short oligonucleotide adapters containing an overhanging "T" base and universal PCR primer regions are ligated to the A-tailed DNA molecules. PCR using universal primers is performed to amplify all successful ligation reactions. The resulting NGS library is denatured and incubated with target enrichment probes for approximately 16 hrs. Next, a series of washes are performed to remove DNA that did not hybridize probes. This is followed by elution of the enriched DNA and a final PCR [10].

Several factors are critical when designing methods for rare variant detection using NGS. Among these is accurate population sampling, which is dependent on efficient NGS library conversion. A critical step in NGS library conversion is the ligation step, where adapters with a "T" base overhang are ligated to sample DNA with "A" base overhangs. This step determines how many unique DNA molecules will be present in the final library. If a representative sampling is not obtained due to poor ligation efficiency, low frequency mutations may not be converted into the NGS library and thus they will be absent from the sequence data [14-15].

Another critical factor that should be considered for rare variant detection is error suppression. Rare variants occur at a similar frequency as errors introduced by sample processing and sequencing enzymes. The Duplex Sequencing method was the first to describe the inclusion of unique molecular identifiers (UMIs), or barcode sequences of 8 to 12 bp, into NGS adapters so that the ligated fragment is flanked by UMIs [15-16]. The UMIs are used to make barcode families consisting of all DNA fragments containing the same flanking UMI sequences. A single strand consensus sequence (SSCS) is generated for each barcode family from read 1 and read 2, which allows variants that are not present in the majority (e.g., 90%) of the reads to be removed. The error correction is further enhanced by generating a double strand consensus sequence (DSCS) by eliminating variants that are not present in both SSCSs that share the same UMIs. This approach is effective at error suppression, but suffers from two issues. First, it is not true duplex sequencing because only one strand is captured and sequenced on the NGS instrument. Second, incorporating UMI sequences into NGS adapters at the point of ligation requires a special adapter synthesis protocol that generates adapters with poor ligation efficiency, which leads to population sampling bias [17].

A second method referred to as integrated Digital Error Suppression (iDES) uses adapters with short UMI sequences that maintain high ligation efficiency [17]. Like Duplex Sequencing, the iDES method also generates duplex sequences using SSCSs and DSCSs, but the authors observed the UMIs were only capable of eliminating a limited number of errors. This was due to the introduction of artifacts during the extended hybridization time at 65° C. required for probe-based target enrichment. The major artifact observed was G>T mutations and the authors observed increased G>T mutations with increased hybridization times [12]. The introduction of G>T artifacts has been previously reported by Costello et al. and determined to be caused by the oxidation of guanine to form 8-oxoguanine [18]. The iDES method incorporates an in silico method to eliminate these artifacts, referred to as "polishing". Roche commercialized the iDES technology as Avenio ctDNA analysis kits that include the molecular biology reagents, computer hardware, and specialized bioinformatics pipeline, although only a limited number of gene panels are available and custom gene panels cannot be analyzed using the iDES bioinformatics pipeline. This is due to the fact the polishing step requires generating a gene panel-specific error profile that must be empirically determined. As a result, the bioinformatics pipeline relies on the error profile of a limited number of gene panels, which severely limited its applications.

The present invention includes novel technologies that resolve these issues, including UMI adapters with high NGS conversion efficiencies combined with target enrichment methods that limit sample oxidation and a unique sequencing strategy for error suppression.

SUMMARY OF THE INVENTION

The object of the present invention is to provide compositions, reagents, and methods for isolating both random and specific nucleic acid regions within a sample and simultaneously attaching engineered NGS adapter molecules with UMIs that facilitate analysis on NGS systems. Here, "engineered" refers to non-naturally occurring nucleic acids that have been designed, i.e., engineered, to provide a series of discrete, functionally independent regions. These novel engineered compositions and methods allow high efficiency target enrichment and improved error suppression. A number of representative compositions, reagents, and methods are described that achieve this objective.

The first aspect of the invention involves directional capture through hybridization of two sequences in an engineered dual adapter probe that are complementary to a target region in the nucleic acid sample. Unlike traditional probe-based capture, which utilizes one or multiple long probes of approximately 120 bp that span the target and capture single-stranded DNA, the current invention utilizes homology regions (HRs) targeted at the 5' and 3' regions of the double-stranded DNA target. The resulting captured dsDNA library fragments are flanked by UMIs and NGS adapter sequences in a closed circular DNA molecule. Nucleic acid amplification, for example, by PCR or by an isothermal process such as rolling circle amplification (RCA) or recombinase polymerase amplification (RPA), using primer(s) that hybridize to the NGS adapter sequences generate a final NGS library ready to load onto an NGS system. Moreover, probe sequences can be designed to capture an engineered sequence, such as an NGS adapter sequence, allowing capture of an existing NGS library. If the dual adapter molecule contains an origin of replication and an antibiotic resistance (or other selectable marker) gene, the NGS library created from a precious sample (such as a depleted tumor block or ctDNA sample) may be archived in, for example, bacteria, yeast, or phage.

A second aspect of the invention involves directional capture through hybridization of one sequence in an engineered dual adapter probe that is complementary to a target region in a nucleic acid sample. By only targeting the 5' or 3' region (and not both), unknown sequences that are adjacent to known sequences, such as those found in gene fusions, may be identified after the fragment is captured and sequenced.

A third aspect of the invention involves enriching target sequences by using engineered NGS adapters that include UMIs and HRs that target specific sequences. Combinations of engineered adapters with HR pairs that target both the 5' and 3' ends of a target sequence are used to hybridize the desired nucleic acid. This is similar to the first aspect of the invention except the 5' and 3' HR sequences are on separate molecules and not physically linked.

A fourth aspect of the invention involves the isolation of random double-stranded nucleic acid using an engineered dual adapter molecule containing topoisomerase binding sites instead of target specific sequences. Similar to the first method, the resulting captured dsDNA library fragments are flanked by UMIs and NGS adapter sequences. Since the captured nucleic acids exist as circular dsDNA, recombinase proteins, such as RecA or UvsX (or similar proteins), may be used for target enrichment to selectively isolate nucleic acid regions of interest. Recombinase proteins can form nucleofilaments with single-stranded oligonucleotide probes. The nucleofilament can form a displacement loop (D-loop) with dsDNA that is highly stable with circular dsDNA. The D-loop is formed by hybridization of the oligonucleotide with a complementary strand in the target dsDNA, forming a triplex. When used with oligonucleotides linked to an affinity tag, such as biotin, the triplex DNA, formed by the oligonucleotide and circular dsDNA dual adapter molecule containing the target nucleic acid sequence, can be selectively isolated from a mixture and sequenced. Recombinase-mediated target enrichment can be performed rapidly (10-20 min) at low temperature (37° C., isothermal), so nucleic acid oxidative damage is limited, which reduces the number of artifacts or errors in the sequence data that may be introduced if traditional probe-based target enrichment is performed at 65° C. [19-21].

Another aspect of the invention involves attaching topoisomerase to engineered, UMI-containing NGS adapters. Adapters are synthesized using a novel approach that uses a combination of oligonucleotides, DNA polymerase and ligase to yield engineered adapters containing UMIs and topoisomerase binding sites. Upon exposure to topoisomerase, the enzyme becomes transiently trapped on the adapter until it encounters A-tailed sample DNA, whereby the adapters become covalently attached to the 5' and 3' ends of the sample nucleic acid. Or, topoisomerase may be trapped on the adapters until ready for use [22-24].

Yet another aspect of the invention involves enriching target sequences by using single-stranded engineered probes that contain UMIs and adapter sequences flanking the target specific sequences. Upon hybridization of the complementary target sequence, non-hybridized sequence is removed and DNA polymerase is used to generate the complementary strands of the UMIs and adapter sequences, thus negating the need to use short oligonucleotide adapters containing double-stranded unique molecular identifiers.

The final aspect of the invention concerns a unique bioinformatics-based error detection process and nucleic acid sequencing instrument made possible by other aspects of the invention since they allow both strands of the target DNA molecule to be captured from a mixture. Current sequencing instruments only analyze one strand. To take advantage of the dsDNA capture, a nucleic acid sequencing instrument that allows both captured strands to be analyzed independently will increase error suppression efficiency when using a bioinformatics strategy that uses both data sets.

The foregoing and other objects, features and advantages of invention will be apparent from the following detailed description, figures, and appended claims.

BRIEF DESCRIPTION OF DRAWINGS

FIG. 2A shows a schematic of an engineered Dual Adapter probe with one HR region to capture gene fusions. Dual Adapter probes can be used to detect gene fusions by targeting either the 5' or 3' region of the gene and using a combination of homologous sequence hybridization and blunt end ligation to capture the gene fusion.

FIG. 2B shows a schematic of an engineered Dual Adapter fusion probe hybridized to a target mRNA. Reverse transcriptase primes off the HR1 region for 1st strand synthesis. RNAseH may be used to remove the mRNA from the RNA/cDNA duplex (not shown).

FIG. 2C shows a schematic of 2nd strand synthesis of the gene fusion using random hexamers and DNA polymerase. Taq DNA ligase is used to seal the backbone, generating a linear dsDNA molecule.

FIG. 2D shows a schematic of blunt end ligation using T4 DNA ligase and polynucleotide kinase.

FIG. 2E shows a schematic of the final circular dsDNA molecule consisting of the Dual Adapter Probe and cDNA of the target gene fusion. Primers that bind to AS1 and AS2 are used to generate the final NGS library, for example, by PCR, RCA or RPA amplification.

FIG. 4A shows a schematic of engineered Topoisomerase (TOPO) Dual Adapter molecule. Topoisomerase-based UMI-adapter attachment paired with recombinase-mediated target enrichment. Engineered TOPO Dual Adapter molecules contain topoisomerase binding sequences CCCTT instead of HR domains. Topoisomerase facilitates covalent joining of random A-tailed nucleic acids to the Dual Adapter molecule. A ligase enzyme, for example, Taq DNA Ligase, is used to repair the non-scissile strand nick.

FIG. 4B shows a schematic of the final dsDNA molecule consisting of the sample nucleic acid and Dual Adapter molecule.

FIG. 4C shows a schematic of recombinase-mediated target enrichment with an engineered, circular dsDNA Dual Adapter molecule containing sample DNA. Circular dsDNA Dual Adapter molecules with sample DNA can be combined with nucleofilaments composed to biotinylated oligonucleotides and RecA protein for target enrichment. RecA facilitates hybridization of oligonucleotides to complementary sample nucleic acid in the TOPO-Dual Adapter molecule.

FIG. 4D shows a schematic of eluted circular dsDNA Dual Adapter molecule containing sample DNA. Primers that bind to AS1 and AS2 are used to generate the final NGS library.

FIG. 5A shows a schematic of isothermal or rolling circle amplification (RCA) to amplify a single strand of an engineered Dual Adapter molecule of the invention that contains a sample DNA fragment with a biotinylated primer. Isothermal amplification reactions are high fidelity and can be performed at low temperature (37° C. or less), which will reduce sample artifacts due to oxidation.

FIG. 5B shows a schematic of concatemers generated by RCA. The repeating unit of the concatemer consists: AS1/UMI1/HR1 or TOPO/sample DNA/HR2 or TOPO/UMI2/AS2.

FIG. 5C shows a schematic of the ssDNA concatemer attached to a streptavidin bead for purification and isolation.

FIG. 5D shows a schematic of individual ssDNA units from the concatemer that were formed by digestion with a restriction or nicking enzyme that recognizes the sequence in the hairpin. These ssDNA molecules may be loaded directly on to the sequencer.

FIG. 6A shows a schematic of engineered HR Adapters, which consist of two oligonucleotides of different lengths that contain both non-complementary and complementary regions, wherein the complementary regions are hybridized together. One oligonucleotide contains the AS1 site at the 5' end, which does not have a complementary sequence and remains single-stranded after hybridization, adjacent to a sequence that has a complementary sequence at the 3' end and is double-stranded after hybridization. The second oligonucleotide contains the complementary sequence to the first oligonucleotide to form a double-stranded region flanked by two single-stranded regions; AS2 at the 3' end and UMI1-HR1 at the 5' end. This first adapter is used with a second adapter containing UMI2 and HR2 homology region to capture a specific sequence (DNA, cDNA, etc.) in a sample. Like the Dual Adapter probe technology, the HR1 and HR2 regions are homologous to target regions and will hybridize to single-stranded DNA.

FIG. 6B shows a schematic of sample DNA that has been treated with an enzyme(s) with exonuclease activity. Single-stranded regions hybridize to complementary HR regions in the Dual HR Adapters. DNA polymerase extends the 3' ends of the adapters to generate the reverse complement of the UMI1 and UMI2 sequences and any single-stranded regions in the target DNA. Taq DNA ligase seals the gaps between adjacent molecules, which results in the entire sense and antisense strands each becoming one covalently linked molecule, and the two molecules are hybridized together.

FIG. 6C shows a schematic of the final captured DNA sequence with adapter sequences covalently attached.

FIG. 6D shows a schematic of PCR products generated from amplification using primers that hybridize to AS1 and AS2.

FIG. 7A shows a schematic of engineered TOPO UMI adapters. Adapters are constructed by annealing 4 oligonucleotides (Oligo 1-4). Oligo 1 may consist of standard sequence found in Illumina's Universal adapter (NGS Adapter Sequence 1: AS1). Oligo 2 may consist of standard sequence found in Index Adapters (NGS Adapter Sequence 2: AS2), but is extended to include a UMI sequence (12 bp in this example) followed by the sequence GGGA. Oligo 3 contains the topoisomerase binding site CCCTT plus additional sequence that is complementary to Oligo 4. Oligo 4 contains sequence that is complementary to Oligo 3 except the first 4 nucleotides of the topoisomerase sequence (CCCT). Alternatively, longer oligos can be used to assemble TOPO dual adapter molecules, whereby Oligo 1 and 2 may be an extended length and hybridize in a staggered manner such that the 5' UMI1 region of Oligo 2 is single-stranded and 5' UMI2 region of Oligo 1 is single-stranded (not shown). Oligos 3 and 4 hybridize in a similar manner at either end of the extended, staggered Oligo 1/Oligo 2 complex.

FIG. 7B shows a schematic of DNA polymerase extending Oligo 1 to generate the complement of the UMI sequence in Oligo 2. Taq DNA ligase is used to covalently link Oligo 1 to Oligo 3.

FIG. 7C shows a schematic of topoisomerase binding the topo binding site CCCTT. Topoisomerase cleaves the phosphate backbone located 3' to the CCCTT sequence.

FIG. 7D shows a schematic of topoisomerase trapped on the CCCTT sequence. Since Oligo 2 and Oligo 4 are not covalently linked, a double-stranded DNA oligo consisting of Oligo 4 and part of Oligo 3 (3' to the CCCTT sequence) separate from the adapter (leaving group). Topoisomerase cannot dissociate from the CCCTT sequence until it cleaves a second phosphodiester linkage between neighboring nucleotides on the complement strand. This is achieved when A-tailed DNA fragments are combined with the Dual Adapter TOPO adapters. A ligase enzyme, for example, Taq DNA Ligase, is used to repair the non-scissile strand nick.

FIG. 7E shows a schematic of two engineered TOPO adapters attached to a sample DNA fragment. The A-tailed sample DNA hybridized to the overhanging T from the CCCTT sequence. Topoisomerase covalently links the adapter to the sample DNA and dissociates.

FIG. 8A shows a schematic of a capture and adapt (CAAD) probe. CAAD probes are single-stranded oligonucleotides (either DNA or RNA) that contain an AS1, UMI1, a single target homology region approximately 120 bp, UMI2 and AS2 anchored to a streptavidin bead at the AS2 site. The AS1 sequence contains multiple phosphorothioate bonds to confer resistance to enzymatic exonuclease activity.

FIG. 8B shows a schematic of a piece of single-stranded sheared genomic DNA binding the CAAD probe. The 5' and 3' regions of the genomic DNA that are not complementary to the CAAD probe do not bind to the probe.

FIG. 8C shows a schematic of Mung Bean Nuclease removing the 5' and 3' overhangs (i.e. the non-complementary regions that do not bind the CAAD probe). Other nucleases can be used that halt ssDNA exonuclease activity when a double-stranded region is encountered.

FIG. 8D shows a schematic of the CAAD probe hybridized to the complementary regions of the target DNA, generating a double-stranded molecule flanked by single-stranded regions that include AS1, UMI1, UMI2 and AS2. DNA polymerase is added to generate the reverse complement of the AS1, UMI1, UMI2 and AS2 sequences. Since DNA polymerase activity is limited to the 5' to 3' direction and requires a double-stranded region for priming, a small primer complementary to AS2 it required to generate the complement to AS2 and UMI2.

FIG. 8E shows a schematic of the CAAD probe hybridized to the full length target DNA containing AS1, UMI1, UMI2 and AS2 sequences.

FIG. 8F shows a schematic of the eluted target sequence containing AS1, UMI1, UMI2 and AS2. The eluted fragment can be PCR amplified using primers complementary to AS1 and AS2 and sequenced on an NGS system. Note: Uracil may be incorporated into the CAAD probe, which allows probe digestion using UNG prior to PCR amplification.

DETAILED DESCRIPTION OF INVENTION

Figure 1A:
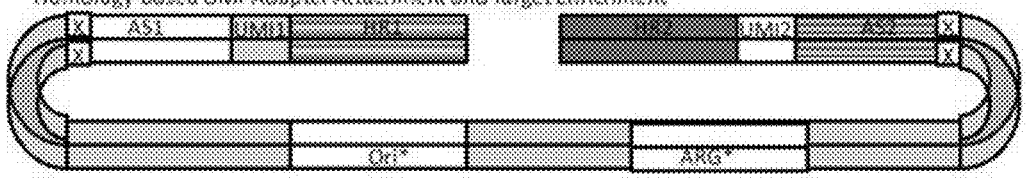
FIG. 1A shows a schematic of a representative Dual Adapter Probe—Homology-based UMI adapter attachment and target enrichment approach according to the invention. Engineered Dual Adapter probes contain all the functional regions for target enrichment and amplification for NGS analysis. The engineered molecules consist of NGS Adapter Sequence 1 (AS1), unique molecular identifier 1 (UMI1), Homology region 1 (HR1), homology region2 (HR2), unique molecular identifier 2 (UMI2) and NGS Adapter Sequence 2 (AS2). Dual Adapter probes may also contain a selectable marker, such as antibiotic resistance, and an origin of replication so the probes may be transformed into bacteria (or other microorganism) after sample nucleic acid has been captured into the probe. This allows NGS libraries to be archived, for example, in the bacteria. Dual Adapter probes target and capture nucleic acid in a directional manner relative to the AS1/UMI1 and AS2/UMI2 sequences and can be designed to capture target nucleic acid in the sense (5' to 3') or antisense (3' to 5') direction. Dual Adapter probes also contain tandem restriction or nicking enzyme sequence that form dsDNA stem-loops or hairpins in ssDNA, which allows cleavage of concatemers following isothermal amplification of the probe after the target is captured.

The present inventions describe methods to improve unique molecular identifiers (UMI) synthesis and incorporation into NGS libraries, with some methods also facilitating simultaneous target enrichment. The first invention combines engineered NGS adapter attachment and target capture into one step by using a double-stranded molecule containing two probe sequences (flanked by UMIs and NGS adapter sequences) that hybridize to the 5' and 3' regions of a target sequence. Upon hybridization, the target sequence is covalently attached to the probe sequences, forming a circular double-stranded DNA molecule (FIG. 1). This two molecule reaction has a higher efficiency than traditional ligase-mediated adapter attachment of traditional NGS preparation. The present invention leverages technology originally developed for seamless cloning or to assemble multiple linear DNA fragments into a vector. These methods include Gibson [25-26], NEBuilder HiFi DNA Assembly, Seamless Ligation Cloning Extract (SLiCE) [27] and Sequence and Ligation Independent Cloning (SLIC) [28], and work by using an exonuclease or DNA polymerase (in the absence of dNTPs) to bind dsDNA and remove nucleotides to generate single-stranded regions at the ends of the target molecule(s) and vector. If two linear molecules are incubated together that have complementary ends (target genes can be PCR amplified to include about 20-25 bp of vector sequence at the 5' and 3' ends), the molecules will hybridize, form dsDNA and stop exonuclease activity (note: protocols that use the exonuclease activity of DNA polymerase require the addition of CTP to stop the exonuclease activity). Next, DNA polymerase primes off the hybridized regions and produces the complementary strand by extending the 3' end of the hybridized DNA. Finally, some methods use a DNA ligase (e.g., Taq DNA ligase) to seal the backbone by catalyzing the formation of a phosphodiester bond between the 5' phosphate and 3' hydroxyl of the adjacent DNA strands [26-29]. All methods transform the reaction into *E. coli* (where gaps are repaired in vivo [28]) and involve screening individual clones to isolate the desired the product.

In one embodiment of the current invention, these seamless cloning technologies are leveraged, but rather than assemble multiple linear DNA fragments or a single target gene into a vector, the present invention describes the creation of engineered dsDNA Dual Adapter molecules that capture target sequences (i.e. exons, hotspot regions in genes, intronic regions, etc.) and simultaneously attach UMI and NGS adapter sequences. The captured nucleic acids are then amplified using primers that anneal to the NGS adapter sequences using PCR or isothermal amplification. The amplified products are then loaded directly onto an NGS sequencer. Dual Adapter Probe (DAP) is a novel technology that combines target-enrichment and NGS library preparation into one step. It increases efficiency of double-stranded UMI incorporation as hybridization of 20-25 bp complementary regions between DAP and target molecules is a more efficient process than ligation-based T/A attachment of adapters. DAPs also capture both strands of a target and can be designed to capture targets in both orientations. This feature is used in a novel error suppression strategy that should reduce artifacts and increase overall accuracy compared to current methods.

DAPs have several functional groups. First, DAPs contain a region of homology sequence (Homology Region 1=HR1) located at or 5' (or upstream) to the desired target DNA and a second region of homology (Homology Region 2=HR2) located at or 3' (or downstream) to the desired target DNA. The HR1 and HR2 regions are flanked by UMIs, which consist of at least 2 base pairs of random nucleic acid sequence and NGS adapter sequences 1 and 2 (AS1 and AS2) that bind primers for existing NGS platforms. For example, NGS adapter sequences containing partial P5 and P7 sequences used for Illumina NGS platforms (Note: primers used to amplify the captured DNA contain the full length P5 and P7 sequences, which allow attachment and amplification on the flowcell). DAP molecules may also include all components necessary to propagate in bacteria (i.e. *E. coli*) or other microorganism under antibiotic selection (i.e. Ampicillin) or other selection methods (FIG. 1A). The ability to transform NGS libraries into bacteria allows archiving of NGS libraries that may have come from a precious source. For example, nucleic acid extracted from an FFPE block with minimal or no tissue remaining.

Figure 1B:
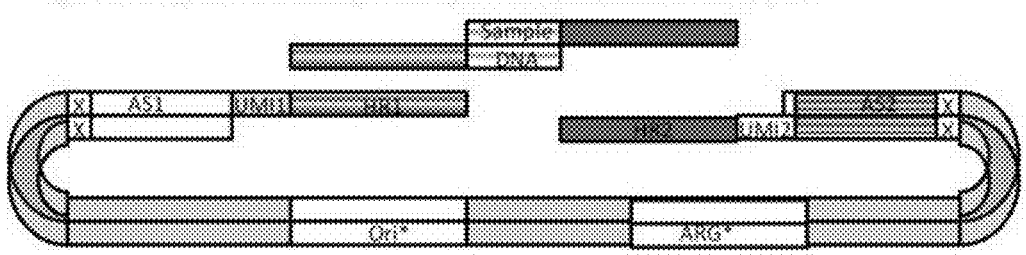
FIG. 1B shows a schematic of engineered Dual Adapter molecules (or probes) and sample nucleic acid after treatment with an enzyme with exonuclease activity (exonuclease or DNA polymerase in the absence of dNTPs), which generates single-stranded ends of the dual adapter and sample nucleic acid.
Figure 1C:
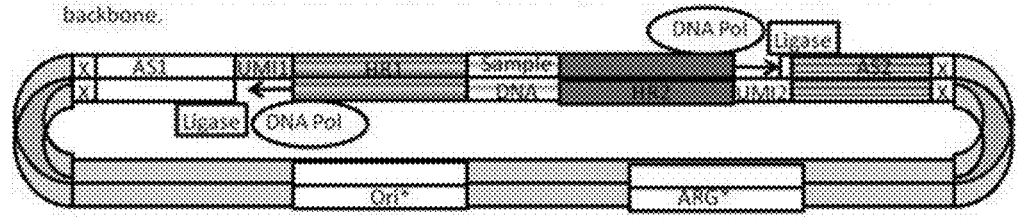
FIG. 1C shows a schematic of an engineered Dual Adapter probe incubated with sample DNA that contains homologous regions to HR1 and HR2 of the engineered adapter molecule. The complementary regions hybridize, leaving single-stranded regions, which are filled in by DNA polymerase. A suitable ligase enzyme, for example, Taq DNA ligase, seals the backbone.
Figure 1D:
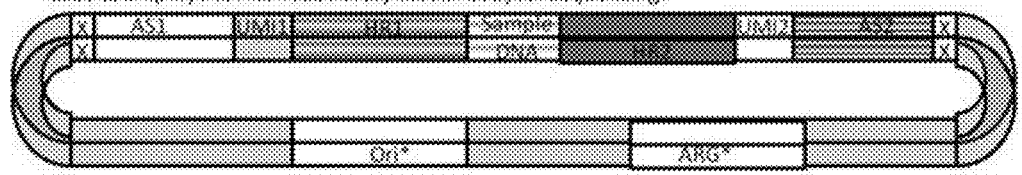
FIG. 1D shows a schematic of the final dsDNA molecule consisting of the Dual Adapter probe and target nucleic acid. Primers that bind to AS1 and AS2 may be used to generate the final NGS library that is ready to be loaded on to a sequencing instrument. Or, rolling circle amplification (RCA) may be used to generate ssDNA concatemers of the circular molecular, which may be separated by digestion of double-stranded stem-loop/hairpin structures containing a restriction or nicking enzyme sequence. Other nucleic amplification processes, for example, recombinase polymerase amplification (RPA), may also be employed.

The workflow for target enrichment using DAPs is similar to methods used for seamless cloning. First, the DAP molecules are treated with exonuclease or DNA polymerase (without nucleotides) to generate single-stranded regions. For example, T5 Exonuclease binds to dsDNA and removes nucleotides in a 5' to 3' direction, leaving single-stranded 3' regions of DNA. Likewise, the sample DNA is treated with exonuclease or DNA polymerase (without nucleotides) to generate single-stranded regions. Next, the DNA molecules with single-stranded ends are incubated under conditions that facilitate hybridization of the complementary single-stranded regions (FIG. 1B). One example of a combination of enzymes/buffer includes, but is not limited to, DNA polymerase and Taq DNA ligase. DNA polymerase fills in the single-stranded regions generated by T5 Exonuclease that flank the DAP molecule/target DNA double-stranded complex and Taq DNA ligase seals the gaps between adjacent fragments (FIG. 1C). Some enzyme mixes, such as NEBuilder HiFi DNA Assembly kit, can remove any non-homologous DNA that is 3' to the DAP molecule/target DNA double-stranded complex, allowing capture of target DNA containing additional sequence outside the region that is complementary to the HR regions. The final product is a circular dsDNA molecule containing the target region of interest flanked by the UMI and NGS adapter sequences (FIG. 1D).

The next step involves either PCR or isothermal amplification. For PCR amplification, target DNA is amplified using primers that bind AS1 and AS2. The PCR products amplified from the DAP molecules contain all sequences necessary for NGS and can be loaded directly onto the sequencer. All reads will be directional since target enrichment is facilitated by different homologous regions targeting the region of interest. Probes can also be designed to capture regions of interest in both orientations. For isothermal amplification, RCA or RPA may be used. For RCA, only the AS1 primer is used and only this single-stranded molecule is loaded on the sequencer. Data can be generated from the forward and reverse strand if the target is captured in both orientations. RPA is similar to PCR and amplifies both strands, but does not require temperature cycling and generates product at low temperature.

In another embodiment, DAPs can be designed to target only one region of a nucleic acid molecule by including only one HR sequence in the probe. The HR1 target region is captured through hybridization and the other end of the target molecule is ligated to the probe through blunt end ligation. This strategy is ideal for detecting gene fusions in cases where only one of the fusion partners is known. The known fusion partner is captured by hybridization of the HR1 probe sequence. The other end of the nucleic acid molecule (DNA, cDNA, RNA, etc.) is linked to the probe through ligation. These modified DAP molecules are referred to as Fusion DAP and include only one HR and UMI sequence (FIG. 2A). Gene fusions are captured through hybridization of mRNA (or cDNA) to HR1, followed by reverse transcription (or DNA polymerase for cDNA) of the captured mRNA using the HR1 probe sequence as the primer to generate cDNA (FIG. 2B). Next, RNAse H degrades the mRNA molecule that is hybridized to the cDNA and DNA polymerase, poly-T oligos (or random hexamers) and DNA ligase are added to generate the complementary strand. An oligonucleotide complementary to the AS2 region is also included to generate dsDNA in the AS2 that was converted to single strand from exonuclease activity (FIG. 2C). End repair, phosphorylation of ends and ligation complete capture of the double-stranded cDNA molecule (FIG. 2D-2E). Finally, amplification of the cDNA using primers that bind AS1 and AS2 generate PCR products that are ready to be sequenced on an NGS sequencer. Alternatively, the cDNA is amplified using RCA or RPA.

A key aspect of the invention is the synthesis method of the DAP molecules, which allow efficient synthesis of double-stranded UMI sequences using PCR. DAP molecules are synthesized using a PCR template molecule consisting of partial or complete NGS adapter sequences located at the 5' and 3' ends of a linear dsDNA molecule. For example, partial or complete P5 and P7 sequences. The 3' primer is designed to anneal to AS1 and includes both the UMI1 and HR1 sequences as a 5' tag. Likewise, the 5' primer is designed to anneal to AS2 and includes both the UMI2 and HR2 sequences as a 5' tag. The PCR reaction amplifies the entire molecule, including the reverse complement of the HR and UMI sequences.

Figure 3:
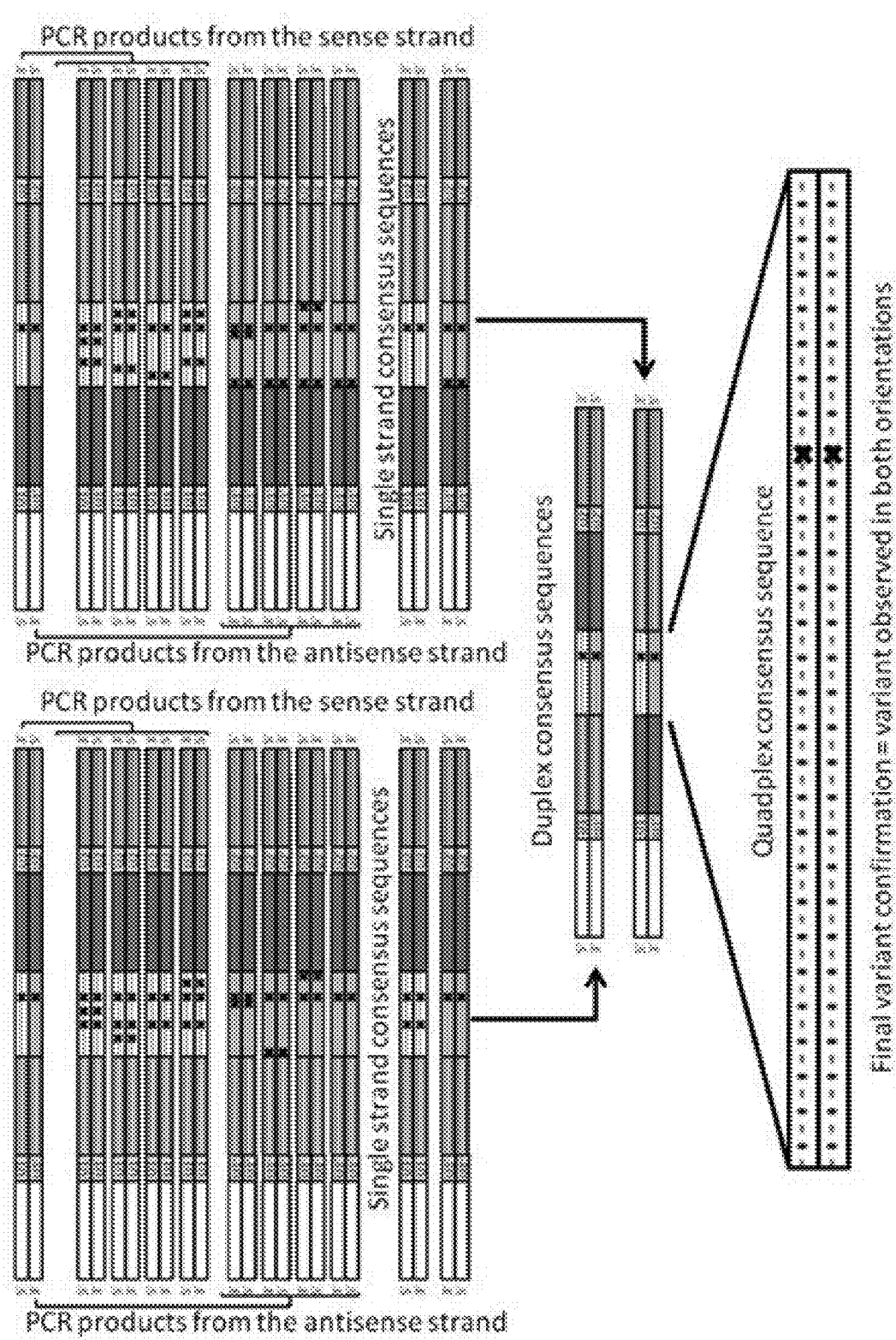
FIG. 3 shows a schematic for the error suppression strategy using the UMI sequences that flank the target DNA. First, UMI pairs are used to generate single strand circular consensus sequences (SSCS). The present invention generates two independent datasets by capturing and sequencing both the sense and antisense molecules from the same target. The independent datasets can be matched up to generate SSCSs since they have complementary UMI sequences. This strategy may increase error detection as errors generated during bridge amplification and emPCR will readily be identified since each molecule will undergo these processes independently. A double-stranded consensus sequence (DSCS) can be generated from the SSCSs. This process can be conducted for target DNA captured in the forward and reverse orientations when using Dual Adapter probes with HR domains to further filter out errors=Quadplex consensus sequence.

The invention also consists of a sequencing strategy and sequencing instrument that generates data from both the sense and antisense strands independently. In current NGS platforms (Illumina and Ion Torrent), only one strand is captured on a flowcell or bead by hybridization to an oligonucleotide that is complementary to adapter sequences on the isolated DNA. This strategy entails a sequencing platform with two separate oligonucleotides with unique sequence; one is complementary to the sense strand of the adapter and the other is complementary to the antisense strand of the adapter so that both the antisense and sense molecules are captured and sequenced. The incorporation of UMIs combined with sequencing both strands of the target in both orientations allows for unprecedented error detection. First, UMI pairs are used to generate single strand circular consensus sequences (SSCS) for data from both the sense and antisense strands. This is done by grouping all sequences flanked by the same UMIs and eliminating variants not present in a majority of the sequence. For example, variants that are not present in at least 90% of all sequences with the same UMI pair are removed. This process is conducted for both the sense and antisense datasets. Next, a double strand consensus sequence (DSCS) can be generated by comparing the SSCSs of the sense and antisense datasets. This can be accomplished because the UMI sequence of the antisense dataset is the complementary sequence to the sense dataset. This strategy may increase error detection as errors generated during bridge amplification and emPCR will readily be identified since each molecule will undergo these processes independently. Further error reduction can be performed by comparing datasets from the forward and reverse consensus sequences for targets that were captured in both the forward and reverse orientations (Quadplex consensus sequence—FIG. 3).

In another embodiment of the invention, which is referred to as Topoisomerase Dual Adapter technology (TOPO-DAT), topoisomerase is used to attach sample nucleic acid to the dual adapter molecule. TOPO-DAT molecules do not have HR1 and HR2 groups and can be used for capturing random double-stranded nucleic acid (i.e. DNA, cDNA, etc.) similar to standard NGS library preparation protocols. The advantage of TOPO-DAT is similar to standard DAP technology in that 1) adapter attachment efficiency is enhanced and 2) efficient incorporation of double-stranded UMIs into the final NGS library.

When topoisomerase protein binds to dsDNA at the sequence (C/T)CCTT, it cleaves the adjacent phosphodiester bond by forming a stable covalent adduct with a tyrosyl residue (Tyr-274) and the 3' phosphate of the last thymine in the consensus sequence in a reversible reaction. Lack of a phosphodiester bond on the non-scissile strand in close proximity to the cleaved scissile strand (and close to the end of the DNA molecule) allows topoisomerase protein to be trapped onto the DNA as the small fragment of dsDNA dissociates, removing the substrate for the reverse reaction. When exposed to sample dsDNA, topoisomerase catalyzes the joining of the two molecules if the 5' ends of the sample DNA are hydroxylated and singled-stranded overhangs (if any) are complementary [22-24].

Accordingly, TOPO-DAT molecules are engineered to contain the topoisomerase binding sites CCCTT at close proximity (10-20 bp) to each end of the dsDNA molecule. In addition, a single strand nicking enzyme sequence is incorporated into the 10-20 bp region in the complement strand and positioned to generate a single thymine base overhang when the TOPO-DAT molecule is exposed to a single strand nicking enzyme followed by topoisomerase in a sequential manner [31]. The resulting topoisomerase charged dual adapter molecule can be linked to sample dsDNA that has an overhanging adenine base (i.e. A-tailed), yielding a library flanked with UMIs and NGS adapter sequences (FIGS. 4A and 4B). In some embodiments, the UMI-NGS library may be PCR amplified using primers that hybridize to AS1 and AS2. The PCR products can be sequenced directly as the primers and NAS sequences contain all sequences necessary for NGS.

In some embodiments, the resulting UMI-tagged library can be subject to probe-base capture protocols, including recombinase-mediated target enrichment, such as RecA mediated target enrichment [20-21]. The RecA protein is required for DNA repair and homologous recombination in *E. coli* and binds ssDNA strongly in long clusters to form a nucleofilament. In the presence of ATP, it can simultaneously bind ssDNA and dsDNA and catalyze a DNA synapsis reaction between the dsDNA and a ssDNA molecule that has a complementary sequence forming a triplex. These triple-stranded structures are referred to as displacement loops, or D-loops, and are an intermediate structure that undergoes further recombination in vivo [30-33]. RecA protein can mediate both homologous pairing and/or strand exchange between appropriate DNA molecules in in vitro homologous recombination assays [34-35]. The strand exchange reaction can be blocked in vitro by ATP-γ-S, a non-hydrolyzable form of ATP. The resulting triple-stranded hybrid structures are stable when RecA is removed from D-loops formed with closed supercoiled circular dsDNA [33,36]. This feature can be exploited for target enrichment when NGS libraries are generated using Dual Adapter molecules that form circular DNA molecules (FIGS. 4C and 4D). In some embodiments, the circular TOPO-Dual Adapter NGS library may be supercoiled in vitro by treating with DNA Gyrase or ethidium bromide, or in vivo by transforming into bacteria and isolating supercoiled TOPO-DAT plasmids. The supercoiled library may be incubated with nucleofilaments generated by combining biotinylated oligonucleotide probes (that serve as invasion probes), RecA protein and ATP-γ-S.

In addition to DNA-DNA hybridization, RecA protein can promote RNA-DNA hybridization. For example, RecA protein coated single-stranded DNA can recognize complementary with naked RNA [37]. Therefore, any recombinase which can promote homologous pairing and/or strand exchange between appropriate DNA molecules or between DNA and RNA molecules may be used with TOPO-Dual Adapter technology. Recombinases of the RecA family include RecA in eubacteria, RadA in archea, Rad51 and Dmc1 in eukaryea, and the bacteriophage T4 UvsX protein [38]. RecA-like recombinases have been isolated from many prokaryotes and eukaryotes. For example, such recombinases include, but are not limited to, the wild type *E. coli* RecA protein [39] and mutant forms of *E. coli* RecA protein, such as RecA 803 and RecA 441 [40-41]; T4 UvsX Recombinase [42]; *B. subtilis* RecA protein[43]; *U. maydis* Rec1 protein [44]; *T. aquaticus* RecA analog protein [45-46] and RecA-like protein derived from fission yeast, mouse and human [47]. In a preferred embodiment of the present invention the wild type RecA-protein is used as recombinase alone or in combination with a second recombinase, such as T4 UvsX.

Previous methods for NGS target enrichment using Recombinase protein [21] describe capture of traditional linear dsDNA NGS libraries using 15 to 25mer oligonucleotides complementary to the displaced sequence in the D-loop to stabilize the structure. In contrast, the current invention generates NGS libraries as closed circular dsDNA that do not require stabilizing oligonucleotides. Stabilizing oligonucleotides may be practical when attempting to capture a small number genes, however, they are not practical with attempting a large capture such as a human exome. For example, 2.1 million 60-90mer oligonucleotide probes are required to capture approximately 20,000 genes (64 Mb) that make up the human exome. Based on the previously described method, a minimum of 2.1 million stabilization probes would be required. This number is likely to increase once the capture is optimized and may negatively affect assay performance or commercial viability.

An important aspect of RecA mediated capture is the fact it occurs rapidly (10-20 min) at low temperature (37° C.) using enzyme-guided hybridization with circular dsDNA. In contrast, traditional oligonucleotide-based target enrichment requires DNA denaturing to generate ssDNA and extended hybridization times (4-16 hrs) at elevated temperatures (65° C.). This is a significant advantage when trying to detect rare variants at low frequency as Newman et. al. suggest background errors (i.e. artifacts) may be introduced into sample DNA from extended hybridization times at elevated temperature. The DNA damage is suspected to be caused by oxidation-induced 8-oxo-guanine causing G>T transitions [17-18]. Thus, RecA mediated target enrichment may generate NGS data with fewer artifacts and increase overall sensitivity. Also, combinations of recombinase-like enzymes may be used in the capture in the event some enzymes show a bias in sequence binding.

In another embodiment of the invention, TOPO-DAT (and DAPs) molecules may contain tandem restriction or nicking enzyme sites flanking the NAS sequences, which can form dsDNA hairpins when a single strand is amplified. This allows the option of amplifying TOPO-DAT molecules using isothermal or rolling circle amplification (RCA) following target enrichment. The dsDNA hairpins allow cleavage of the resulting ssDNA concatemers into individual units, which can be loaded directly on the sequencer when full length NGS adapter sequences (i.e. full length P5 and P7 sequences) are incorporated into TOPO-DAT and DAP molecules (FIG. 5). Temperature cycling during PCR has been shown to be the major contributor towards mutations in amplification products [48], so eliminating the need for PCR amplification after capture should improve overall accuracy of the TOPO-DAT/RecA (and DAP) target enrichment approach. The same bioinformatics error suppression strategy may be used for TOPO-DAT/RecA target enriched nucleic acid as both strands are captured and the UMI complements may be matched up if both strands are captured to the flowcell.

A key aspect of the invention is the synthesis method of the TOPO-DAT molecules, which allow efficient synthesis of double-stranded UMI sequences using PCR. TOPO-DAT molecules are synthesized using a PCR template molecule consisting of partial or complete NGS adapter sequences located at the 5' and 3' ends of a linear dsDNA molecule. For example, partial or complete P5 and P7 sequences. The 3' primer is designed to anneal to AS1 and includes the UMI1 sequence, topoisomerase binding site and a leaving group containing a nicking enzyme sequence as a 5' tag. Likewise, the 5' primer is designed to anneal to AS2 and includes the UMI2 sequence, topoisomerase binding site and a leaving group containing a nicking enzyme sequences as a 5' tag. The reverse complement of the UMI, topoisomerase binding site and leaving group sequences are generated during the PCR reaction.

In another embodiment, the dual adapter molecule is synthesized without topoisomerase sites and target fragments are attached to the dual adapter molecule using traditional T/A ligation. The molecules are still synthesized using the PCR method described previously to generate double-stranded UMI sequences flanking the T/A cloning site, but the TOPO and nicking enzyme sequences are replaced by a leaving group containing a type IIS restriction enzyme, such as BmrI type IIs. Similar to TOPO-DAT, this molecule is used to capture random nucleic acid sequences for NGS analysis.

In another embodiment of the invention, two HR sequences (HR1 and HR2) that are homologous to the 5' and 3' regions of a target are included on two separate adapters molecules that also contain UMI and NGS sequences. Similar to other embodiments, DNA polymerase is used to synthesize the reverse complement of UMI sequences. Individually, these HR adapter molecules consist of two oligonucleotides of different lengths that contain both non-complementary and complementary regions, wherein the complementary regions are hybridized together (FIG. 6A). One oligonucleotide contains the AS1 site at the 5' end, which does not have a complementary sequence and remains single-stranded after hybridization, adjacent to a sequence that has a complementary sequence at the 3' end and is double-stranded after hybridization. The second oligonucleotide contains the complementary sequence to the first oligonucleotide to form a double-stranded region flanked by two single-stranded regions; AS2 at the 3' end and UMI1-HR1 at the 5' end. This first adapter is used with a second adapter containing UMI2 and HR2 homology region to capture a specific sequence (DNA, cDNA, etc.) in a sample. Like the DAP technology, the HR1 and HR2 regions are homologous to target regions and will hybridize to single-stranded DNA. DNA polymerase is used to extend the 3' end of the adapters to generate the reverse complement of the UMI1 and UMI2 sequences and any single-stranded regions in the target DNA. DNA ligase is used to seal the backbone (FIG. 6B). The final captured DNA sequence (FIG. 6C) can be PCR amplified using primers that hybridize to AS1 and AS2 (FIG. 6D). These HR adapters are highly suited for droplet based fluidics platforms whereby the HR adapter pairs may be synthesized and incorporated into droplets. Next, droplets are fused with genomic DNA droplets and reaction droplets containing the necessary enzymes and buffer to facilitate homology-based adapter attachment. This approach is very similar to droplet-based PCR for NGS target enrichment [49].

Alternatively, UMI NGS adapters with or without HR regions may be created using RCA. First, a single-stranded synthetic oligo is generated that contains: 1) NGS adapter sequence(s) such as the Illumina adapter sequences P5 and/or P7; 2) random nucleotides that serve as UMI sequences positioned adjacent and 3' to the NGS adapter sequence; 3) an HR domain (optional); 4) a "A" base located 3' to the UMI sequence or HR domain if one is present, and 5) a recognition site for a type IIS restriction enzyme, such as BmrI, that cleaves outside of the recognition site located adjacent to the "A" base such that the enzyme cleaves at the "A" and generates and overhanging "T" base when a dsDNA molecule is generated. Adapters are generated by the following process: 1) the synthetic ssDNA is circularized using a splint ligation strategy or the enzyme circulase; 2) the splint ligation oligo (or other oligo) is used as a primer for RCA to generate a long ssDNA concatemer molecule containing repeats of the features listed above; 3) RCA reaction is stopped and ssDNA is purified; 4) An oligonucleotide containing both a non-homologous region and a region complementary to the NGS adapter sequences hybridize to multiple sites along the ssDNA concatemer; 5) a non-strand displacing DNA polymerases such as T4 and T7 DNA polymerases (gap filling enzymes) are used to generate the reverse complement of the UMI and optional HR sequences, Type IIA restriction enzyme sequence and other sequences located between adjacent hybridized oligos (note: the polymerase will not displace the neighboring oligo containing a non-homologous region that remains single-stranded); and 6) the Type IIA enzyme is added to the reaction to cleave the at the T/A position generating individual Y-shaped adapters with double-stranded UMIs and a single "T" over-hang which can be used in T/A mediated ligation.

In another embodiment of the invention, topoisomerase binding sites and UMIs are incorporated into NGS adapters to produce TOPO UMI adapters. Similar to other embodiments, DNA polymerase is used to synthesize the reverse complement of UMI sequences. Adapters are constructed by annealing 4 oligonucleotides (Oligo 1-4). Oligo 1 may consist of standard sequence found in Illumina's Universal adapter (NGS Adapter Sequence 1: AS1). Oligo 2 may consist of standard sequence found in Index Adapters (NGS Adapter Sequence 2: AS2), but is extended to include a UMI sequence followed by the sequence GGGA. Oligo 3 contains the topoisomerase binding site CCCTT plus additional sequence that is complementary to Oligo 4. Oligo 4 contains sequence that is complementary to Oligo 3 except the first 4 nucleotides of the topoisomerase sequence (CCCT) (FIG. 7A). Alternatively, longer oligos can be used to assemble TOPO UMI adapter molecules, whereby Oligo 1 and 2 may be an extended length and hybridize in a staggered manner such that the 5' UMI1 region of Oligo 2 is single-stranded and 5' UMI2 region of Oligo 1 is single-stranded. Oligos 3 and 4 hybridize in a similar manner at either end of the extended, staggered Oligo 1/Oligo 2 complex. Next, DNA polymerase is used to extend Oligo 1 to generate the complement of the UMI sequence in Oligo 2 and Taq DNA ligase is used to covalently link Oligo 1 to Oligo 3 (FIG. 7B). When topoisomerase binds the CCCTT sequence, it cleaves the phosphate backbone located 3' to the CCCTT sequence (FIG. 7C). Since Oligo 2 and Oligo 4 are not covalently linked, a double-stranded DNA oligo consisting of Oligo 4 and part of Oligo 3 (3' to the CCCTT sequence) separate from the adapter and trap topoisomerase on the adapter (FIG. 7D). Topoisomerase cannot dissociate from the CCCTT sequence until it cleaves a second phosphodiester linkage between neighboring nucleotides on the complement strand. This is achieved when A-tailed DNA fragments are combined with the TOPO UMI adapters (FIG. 7E).

In another embodiment of the invention, long capture probes that are complementary to target regions are created with flanking sequences that consist of UMIs and NGS adapter sequences. These probes are referred to as capture and adapt (CAAD) probes (FIG. 8A). Similar to other embodiments, DNA polymerase is used to synthesize the reverse complement of UMI sequences. CAAD probes are designed to simultaneously capture select sequences from a mixture of DNA molecules and add NGS adapter/primer binding sequences and UMIs to the captured DNA. CAAD probes are incubated with a mixture of DNA molecules and selectively hybridize to their complementary target sequences (FIG. 8B). Following incubation, the hybridized DNA complexes are washed several times to remove non-specific hybridization. Following the washes, the non-hybridized single-stranded DNA flanking the target complementary sequence is degraded using a nuclease, such as Mung Bean nuclease, which can degrade both 5' and 3' over hangs and halts exonuclease activity once it encounters dsDNA (FIG. 8C). Next, DNA polymerase is added to extend the 3' end of captured DNA sequence or AS2 primer sequence (FIG. 8D). As a result, the single-stranded regions containing AS1, UMI1, UMI2 and AS2 sequences flanking the target DNA are converted to dsDNA. Finally, the full-length target sequence flanked with AS1, UMI1, UMI2 and AS2 is eluted from the probe. Alternatively, uracil may be incorporated into the probe during synthesis, which allows the probe to be degraded with UNG, thus preventing probe sequence from being amplified in the subsequent PCR reaction. The captured fragments are PCR amplified with primers compatible with NGS systems. The resulting PCR products can be sequenced on an NGS system (FIG. 8E).

The present invention also includes a complete system consisting of any of the target enrichment/sample preparation inventions listed above, sequencing instrument that can sequence both strands and a bioinformatics pipeline for data analysis. This system may be submitted to the FDA as an in vitro diagnostic (IVD) test for ctDNA, solid tumor DNA/RNA, hematological malignancy DNA/RNA and germline DNA/RNA based assay. The system may also be used for infectious disease detection and organ transplant monitoring.

In one embodiment, all aspects of the invention (DAPs, TOPO-DAT/RecA Capture, HR Adapters and CAAD) can be used to design any gene panel for diagnostic use. Targeted gene panels have become standard tools for cancer diagnostics. These gene panels allow simultaneous gene mutation detection across different cancer types and contain genes whose mutations are associated with a particular FDA approved, off-label or investigational therapy. For example, a panel to capture the approximately 2800 hotspot mutations from 50 oncogenes and tumor suppressor genes in the COSMIC database [50]. In this scenario, probes would target the regions known to harbor hotspot mutations or entire exons that contain the target mutation. Multiple overlapping probes can be designed to capture the entire region. The panel can be used to provide clinically actionable data for solid tumor specimens. For example, if BRAF V600E is detected in a melanoma tumor specimen, a physician can prescribe a BRAF inhibitor such as vemurafenib [51]. In some cases, a biopsy specimens cannot be obtained, so ctDNA specimens are the only option. This is very common for lung cancer patients. The current invention has increased DNA capture efficiency and high mutation detection sensitivity due to advanced error suppressor, so the assay can provide clinically relevant data for ctDNA specimens. For example, if the common lung cancer mutation L858R is detected, the treating physician can prescribe tyrosine kinase inhibitors such as erlotinib [52]. In another embodiment of the invention, a very large gene panel (>300 genes) targeting full exon analysis of genes associated with FDA approved, off-label and investigational drugs is created with the invention. Data from the large panel not only allows for directed therapy options to be discovered, but also total mutation burden, which serves as a positive indicator for response to immunotherapy [53].

In another embodiment, the invention can be used to detect Microsatellite instability (MSI). MSI is a surrogate marker for DNA mismatch repair (MMR) deficiency and the FDA has approved immunotherapy for any tumor type exhibiting MSI [54]. MSI assays analyze repeat regions within the human genome that are susceptible to error due to DNA polymerase strand slippage. Individuals harboring a germline or somatic mutation in a MMR gene that disables this pathway will contain deletions in these repeat regions. MSI assays work by capturing select regions DNA repeats such as BAT25, BAT26, MONO-27, NR-21 and NR-24 and comparing repeat lengths between DNA isolated from the blood and tumor specimen [55]. Due to their repetitive and low complexity nature, these repeat regions are difficult to selectively capture using standard probe-based target enrichment protocols. DAPs may be designed to target the flanking regions located outside the repeats region, hence the efficiency of the target capture should be improved. Moreover, repeat regions are more likely to produce sequencing errors on NGS systems. The unique sequencing strategy and error suppression technology incorporated into DAPs should be able to identify and remove these errors, and provide physicians with more accurate results when determining eligibility for immunotherapy.

In another embodiment, the invention can be used to detect Loss of heterozygosity (LOH). LOH is a condition common in tumors whereby the wild type allele is lost/deleted and only the mutant/inactive copy remains. LOH is very common in individuals with hereditary colon and endometrial cancer (diseases driven by inactivation of the MMR pathway) and often serves as the "second hit" that leads to tumor formation and disease [57]. Determining LOH status of the five MMR genes (MLH1, MSH2, MSH6, PMS2 and EPCAM) and their mutational status is also used to determine eligibility for immunotherapy [58]. Global LOH profiles also serves as a surrogate marker for homologous recombination repair deficiency (HRD), which is a disease driven by inactivation of the homologous recombination DNA repair pathway. Current FDA companion diagnostics analyze tumor LOH status and mutational status of the HRD genes BRCA1 and BRCA2 to determine eligibility for PARP inhibitors in breast and ovarian cancer patients [59-60]. NGS methods for determining LOH requires capturing intronic regions within either the MMR genes to determine LOH status of individual MMR genes, or multiple select introns throughout the genome to generate a global LOH profile. Intronic regions consist of low complexity/repetitive sequence which can pose problems for traditional probe-based capture. DAPs can be designed to capture the flanking regions of the repetitive regions and allow efficient capture for LOH analysis. Moreover, all aspects of the invention (DAPs, TOPO-DAT/RecA Capture and CAAD) can be used to create a panel to provide a global LOH profile and mutational status for MMR and HRD genes for immunotherapy and PARP inhibitor eligibility determination.

In another embodiment, all aspects of the invention (DAPs, TOPO-DAT/RecA Capture and CAAD) can be used to create gene panels for patient recruitment into clinical trials. For example, PARP inhibitors are more effective in patients with a mutation in BRCA1, BRCA2 or have an increased number of LOH regions within their genome [60]. A gene panel that targets these genes and regions can be used to enroll patients in PARP inhibitor clinical trials by analyzing DNA extracted from blood and tumor tissue. Moreover, an extended gene panel can be used for patient stratification and biomarker discovery during and after the clinical trial. Patient stratification includes grouping patients with the same diagnosis and prescription into groups such as drug beneficial and nontoxic, drug non-beneficial and non-toxic, drug beneficial and toxic and drug non-beneficial and toxic. An example panel for non-responders to immunotherapy treatment for biomarker discovery is one that targets the antigen presentation and interferon gamma pathway as mutations in these pathways have been show to facilitate resistance to immunotherapy in melanoma cell lines [61].

In another embodiment, all aspects of the invention (DAPs, TOPO-DAT/RecA Capture and CAAD) can be used to monitor patients diagnosed with ovarian cancer. The majority of patients who have been diagnosed with ovarian cancer will have recurrent disease. In fact, 50% of patients who achieve remission after first-line chemotherapy will experience recurrence of cancer within 3 years. Current methods for detecting recurrent disease include CA-125 blood antigen, x-rays and CT scans [62]. Liquid biopsies have been shown to detect recurrent cancer earlier than these methods. The current invention may be used to design ovarian cancer specific gene panels and used as a surveillance tool to monitor for cancer recurrence. The current invention has higher capture efficiency that provides a more representative sampling of the ctDNA molecule population than current methods. Moreover, the error suppression technology allows the detection of extremely rare variants, thus providing a very high level of sensitivity, which may translate into early cancer recurrence detection.

In another embodiment, all aspects of the invention (DAPs, TOPO-DAT/RecA Capture and CAAD) can be used to monitor patients with heredity cancer syndromes. There are several heredity cancer syndromes with known associated gene mutations. These include hereditary breast and ovarian cancer syndrome, Cowden Syndrome, Lynch Syndrome, Hereditary leukemia and hematologic malignancies syndrome and Li-Fraumeni Syndrome to name a few [63]. These high-risk populations will eventually develop cancer and early detection and treatment increases the likelihood of patient survival. The current invention can be leveraged to create gene panels specific to a hereditary cancer syndrome for ctDNA surveillance to detect early disease. The invention's highly efficient target enrichment and error suppression features can provide the extremely high sensitivity for early disease detection.

In another embodiment, DAPs can be used for T-cell and B-cell repertoire analysis [64-65]. T-cell and B-cell clonal populations can be analyzed by cDNA capture using DAPs. In this scenario, the conserved regions flanking the variable regions in the TCR and BCR genes are targeted with the DAPs. The UMI sequences can be used to generate SSCSs and DSCSs and determine which clonal population has expanded in a patient in response to an antigen or immunotherapy by counting unique clones based on UMI data. Moreover, Fusion-DAPs may also map the diversity of CAR-T integration sites and estimate both the transduction efficiency and copy number of integration events [66]. This is accomplished by targeting the conserved region of the integration cassette with the HR1 domain and determining the neighboring region (genomic integration site), similar to the strategy used for gene fusions.

In another embodiment, the sample DNA is treated with RNA guides in a CRISPR/Cas, TALEN, or comparable system for targeted DNA cleavage. In this scenario, samples would be treated with enzyme and RNA guides for targeted cleavage. A reverse SPRI method may be used to separate cleaved dsDNA from non-cleaved [67]. Or, a biotinylated mutated Cas9 protein that binds target DNA without cleaving may be used to separate the cleaved dsDNA from un-cleaved [68]. The cleaved samples would then be incubated with DAPs that target with the cleaved DNA fragments. Once captured, the target DNA may be amplified and sequenced.

In another embodiment, target DNA is first PCR amplified and then incubated with DAPs that target the PCR products. In one scenario, HR1 and HR2 sequence can be a universal synthetic sequence that is incorporated into the gene specific primers. So, only DAP molecules composed of these specific HR sequences that contain the universal synthetic sequences are required to capture any PCR amplicon containing those sequences. In another scenario, PCR primers are designed to target regions flanking the desired target and DAPs are designed to target regions within the PCR primer regions. As a result of DAP capture, the PCR primer sequences are removed. If the target is PCR amplified in both orientations and DAPs designed to capture in both orientations, sequence data can be generated that is free of both primer and probe sequence if datasets are combined.

In another embodiment, mRNA is converted to cDNA and captured by TOPO-DAT molecules for whole transcriptome analysis. The UMIs can be used for transcript quantification and the high efficiency TOPO-DAT molecules should generate a more diverse mRNA transcript library than ligation-based methods [69]. Moreover, the UMIs will provide superior reverse transcription error identification by generating SSCSs.

In another embodiment, DAPs can be designed asymmetrically to capture difficult/low complexity regions. For example, intronic regions that will be used to determine LOH or large repetitive regions that will be used to measure MSI or elevated microsatellite alterations at selected tetra-nucleotide repeats (EMAST) [70] can have DAPs with HR1 at 20 bp and HR2 at 500 bp to ensure selective capture. Due to the extensive length of HR2, only Read 1 data would be used for analysis as HR2 probe size exceeds typical read lengths.

In another embodiment, the entire DAP containing the target DNA may be sequenced with a long read technology such as the Sequel System from Pacific Biosciences. Currently, long fragments up to 20-30 kb are isolated using long range PCR, but long range PCR is not practical for fragments larger than 30 kb. DAPs may be used for target enrichment of these large DNA fragments. Since DAPs form closed circular molecules upon target capture, the molecules may be transformed into *E. coli* if an antibiotic resistance gene and origin of replication are included in the probe backbone. Next, DAP DNA is isolated and sequenced using a long read sequencing technology, such as Pacific Biosciences Sequel System, as DAPs may be denatured and random hexamers hybridized and loaded onto the sequencer [71]. This method allows for large fragment capture and sequencing without PCR. Large fragments that are too large for long range PCR and traditional target enrichment may be captured and analyzed using this method. This is accomplished by using DAPs that contain a modified 5' or 3' nucleotide at or in the proximity to the terminal nucleotide composed of an affinity tag, such as biotin, that facilitates affinity purification. This allows DAPs to be used in a similar manner as traditional bait capture probes. In this scenario, DAPs with large HR1 and HR2 regions (i.e. 50 bp to 1000 bp) may be used to capture large DNA fragments (20 kb to 50 kb). First, an enzyme with 3' exonuclease activity (such as T4 DNA polymerase in the absence of nucleotides) is used to generate single-stranded HR1 and HR2 regions in the Dual Adapter probe. Next, the probe is incubated with sheared sample DNA in hybridization buffer. Next, the DAPs/DNA complexes are bound to streptavidin beads and washed several times. Next, beads are resuspended in water and heated for 5 minutes at 75° C. to disrupt the biotin/streptavidin interaction and release the DAPs/DNA complex from the streptavidin beads. The supernatant containing the DAPs/DNA complex is treated with one or more enzymes with 5' and 3' exonuclease, such as Mung Bean exonuclease. Alternatively, the heating step can be eliminated as the exonuclease step may release the DAPs/DNA complex from the streptavidin beads. Next, the DNA is purified and either directly transformed into bacteria, which will complete the DAP fragment insertion through in vivo homologous recombination enzymes, or DNA polymerase and Taq DNA ligase may be used in vitro. The closed circular DAPs containing the target DNA may be transformed into bacteria for amplification or amplified using rolling circle amplification. The amplified DNA can be loaded directly on a long read sequencer such as the Pacific Biosciences Sequel System [72].

In another embodiment, DAPs can be used to capture entire transcripts that traditional probe-based target enrich technologies cannot isolate. First, RNA may be isolated and converted to cDNA. Next, DAPs can be designed to capture the first and last exons of a complete transcript or any combination of transcripts to ensure the total molecule length does not exceed the sequencing read length (i.e. exon 1 and exon 6, or exon2 and exon 10, etc.). Multiple probes would be designed to capture several adjacent regions to cover the entire cDNA length. This method can used to detect deep intronic mutations that generate slicing mutations leading to intronic sequence inclusion in the final transcript and premature stop codon introduction [73]. These DAP libraries may be sequenced on long read sequencers such as Pacific Biosciences Sequel System.

In another embodiment, all aspects of the invention (DAPs, TOPO-DAT/RecA-mediated capture or CAAD probes) may be used to monitor transplant rejection. Donor-derived cell-free DNA (ddcfDNA) may be used as a biomarker for allograft rejection. If a donor tissue is rejected, the host immune system destroys donor tissue cells and releases ddcfDNA into the blood stream. Dual Adapter or CAAD probes may be used as a surveillance tool to monitor tissue rejection, evaluate response to anti-rejection therapy and decrease the need for more invasive procedures [74].

In another embodiment, DAPs can be used to detect gene fusions by capturing mRNA or DNA. Gene fusions such as EML4-ALK are common drivers of cancer [75]. Some gene fusions may only have one partner that is commonly found in fusions. DAPs can be designed to target one region of the fusion and facilitate capture of both the known and unknown fusion gene sequences. Following PCR and sequencing of the captured fusion, the fusion partner may be identified. Moreover, whole transcriptome sequencing of full transcripts may identify gene fusions in cancer [76]. As mentioned previously, TOPO-DAT molecules combined with long read sequencing technology can capture and sequence full-length transcripts for fusion discovery.

In another embodiment, target DNA is enriched using traditional single-stranded RNA or DNA probes. The enriched DNA is eluted off the probes as single-stranded DNA and captured using DAPs and the enzymes T5 exonuclease, DNA polymerase and Taq DNA ligase. DAPs can hybridize to ssDNA that has been enriched using traditional oligonucleotide probes. Combining traditional target enrichment with DAPs allows double enrichment, which is beneficial when attempting capture of a small region or number of targets. A double capture can limit off-target sequence isolation and maximize on-target sequence data generation [77].

In another embodiment, DAPs containing an antibiotic resistance gene and origin of replication may be used to archive NGS libraries produced with any NGS library preparation kit. This is accomplished by designing DAPs with HR sequences specific to NGS adapter sequences. For example, the Illumina P5 and P7 sequences. Once the libraries are captured into the DAPs, the library can be transformed into bacteria, propagated and archived by making bacteria glycerol stocks. The ability to archive NGS libraries is a significant advancement in the current state-of-the-art as precious DNA samples isolated from tumor blocks and/or ctDNA samples can be amplified in bacteria and analyzed repeatedly over time. For example, an NGS library created from the last amount of DNA from an FFPE specimen (i.e. the FFPE specimen is now exhausted) may be analyzed using a gene panel with 400 targets in an effort to identify treatment options for a patient. By archiving the patients NGS library, it can be analyzed at a later date with an updated panel that may contain new therapeutic targets. Or, archiving NGS libraries allows pharmaceutical companies with FFPE block and blood biorepositories/biobanks to run sample DNA multiple times on different gene panels without risk of depleting high value specimens (i.e. highly characterized specimens with extensive molecular and clinical data).

In another embodiment, DAPs may be used with microfluidic or droplet-based or reaction miniaturization device/instrument so that sample DNA is diluted such that a limited amount of DNA is captured in each droplet, chamber, etc. and combined with Dual Adapter probes [78]. Bringing target DNA in close proximity with limited competing DNA should enhance homology-based capture with Dual Adapter probes. In addition, HR Adapter technology may be compatible with drop-based fluidics instruments whereby HR Adapter pairs are enclosed in individual droplets. These droplets are then combined with fragmented sample nucleic acid that has been treated with an enzyme with exonuclease activity to generate 5' single-stranded ends.

In another embodiment of the invention, prenatal genetic testing and noninvasive prenatal testing (NIPT) can leverage DAP or TOPO-DA technology for higher efficiency capture which may allow earlier detection than current technologies [79]. Similar to ctDNA, fetal DNA may be isolated from the blood of a pregnant mother. This DNA can be captured using wither DAP or TOPO-DAT/RecA target enrichment and analyzed for mutations and chromosomal abnormalities such as trisomy 21.

Kits for the different variations of the described invention may consist of different components.

In one embodiment, Dual Adapter probes (DAPs), capture and adapt (CAAD) probes or HR Adapters that target different genes (i.e. exons) may be synthesized, pooled and sold as a gene panel. For example, a panel that includes the NCCN genes ALK, APC, BRAF, BRCA1, BRCA2, EGFR, ERBB2, KIT, KRAS, MET, NRAS, PDGFRA, RET, ROS1 and TP53. Alternatively, custom DAPs may be created. The kit comprises the gene panel, enzymes (i.e. exonuclease, DNA polymerase, Taq DNA ligase, etc.), buffers and protocol.

In another embodiment, the DAPs, CAADs and HR adapters and kit components may be manufactured for use with droplet-based fluidics systems available from companies such as Biorad, RainDance and 10× Genomics. Individual DAPs and HR Adapter pairs may be encapsulated into droplets. Likewise, all enzymes and buffers required for homology based DAP and HR adapter attachment are encapsulated into droplets. The droplet-based fluidics systems are capable of merging droplets and regulating temperature to facilitate the appropriate reaction conditions. Droplets can be recovered and DNA extracted and subjected to PCR, RCA, or RPA to generate the final target enriched NGS library.

In another embodiment, Fusion Dual Adapter probes (Fusion DAPs) that target different gene fusions may be synthesized, pooled and sold as a gene fusion panel. For example, a panel that includes gene fusions commonly found in lung cancer ALK, EGFR, MET, BRAF, FGFR, NRG1, NTRK, RET and ROS. Alternatively, custom Fusion DAPs may be created. The kit comprises the gene panel, enzymes (i.e. reverse transcriptase, RNAase H, DNA polymerase, Taq DNA ligase, PNK, ligase, etc.), buffers and protocol.

In another embodiment, DAPs containing an antibiotic resistance gene, origin of replication and HR domains that have homology to NGS adapter sequences may be synthesized and included in a kit for archiving previously generated NGS libraries, ideally pre-target enrichment libraries, so the whole genome is represented. Laboratories with precious DNA samples that have been adapted for NGS can use the kit to archive pre-target enrichment libraries by generating E. coli glycerol stocks and storing at low temperature (e.g., −80° C.). Libraries may be accessed at a later date by amplifying in E. coli. For example, E. coli containing the archived library may be plated out on antibiotic media and plasmid library isolated. Next, the library can be subject to target enrichment using recombinase-mediated target enrichment or it can be PCR amplified using NGS primers and subject to traditional target enrichment. The kit comprises the DAP molecule targeting the NGS sequences, enzymes (i.e. exonuclease, DNA polymerase, Taq DNA ligase, etc.), buffers, competent E. coli cells and protocol. The kit may also contain reagents for performing recombinase-mediated target enrichment and include, for example, RecA and/or UvsX protein, ATP-γ-S, DNA Gyrase, Proteinase K, streptavidin beads and buffers.

In another embodiment, topoisomerase adapted dual adapter technology (TOPO-DAT) molecules or topoisomerase charged NGS adapters may be included in an NGS sample preparation kit. The kit comprises TOPO-DAT molecules or TOPO adapters with NGS sample preparation enzymes and buffers for DNA shearing, end repair, A-tailing, PCR, RCA, or RPA. The kit may also contain reagents for performing recombinase-mediated target enrichment and include, for example, RecA and/or UvsX protein, ATP-γ-S, DNA Gyrase, Proteinase K, streptavidin beads and buffers.

In another embodiment, the TOPO-DAT molecule may not be pre-charged with topoisomerase, but pre-nicked with a nicking enzyme. The kit comprises uncharged TOPO-DAT molecules and the enzyme topoisomerase, as well as NGS sample preparation enzymes and buffers for DNA shearing, end repair, A-tailing, PCR, RCA, or RPA. The kit may also contain reagents for performing recombinase-mediated target enrichment and include, for example, RecA and/or UvsX protein, ATP-γ-S, DNA Gyrase, Proteinase K, streptavidin beads and buffers.

In another embodiment, dual adapter technology (DAT) molecules that utilize standard T/A ligation may be included in an NGS sample preparation kit. The kit comprises DAT molecules with NGS sample preparation enzymes and buffers for DNA shearing, end repair, A-tailing, ligation, PCR, RCA, or RPA. The kit may also contain reagents for performing recombinase-mediated target enrichment and include, for example, RecA and/or UvsX protein, ATP-γ-S, DNA Gyrase, Proteinase K, streptavidin beads and buffers.

EXAMPLES

The following examples are provided solely to illustrate the concept of the present invention and not meant to limit the present invention to the embodiments provided.

Example 1

Dual Adapter Probe (DAP) Generation

Initially, DAPs were generated using the plasmid pUC19 as the backbone. A 2091 bp fragment containing a pUC19 backbone with partial regions of the Illumina sequences P5 and P7 was PCR-amplified using Taq polymerase (from Monserate Biotechnology Group) and standard conditions with the primers P5-L4440+RC (AGATCGGAAGAGCGT CGTGTAGGCTTCCTCGCTCACTGACTCGCT) and P7-pGEX 3' (AGATCGGAA GAGCACACGTCTGCCGG-GAGCTGCATGTGTCAG AGG). This molecule (P5/pUC19/P7) was used as a template in all subsequent PCR reactions used to generate DAPs containing UMIs and homologous regions to target genes. This was accomplished by including UMI1 and HR1 sequences in the first oligonucleotide primer and UMI2 and HR2 sequences in the second oligonucleotide primer as a single-stranded sequence. The primers anneal to the P5 and P7 sequences in the P5/pUC19/P7 molecule. The following primers were used to generate DAPs for:

```
KRAS exon 2:
KRAS_2-seq1-UMI-P5-RC (TCAGTCATTTTCAGCAGGCCTTNNNNNN

NNNNNAGATCGGAAGAGCGTCGTGTAG)

KRAS_2-seq2-UMI-P7-RC (ACTGGTGCAGGACCATTCTTTGNNNNNN

NNNNNAGATCGGAAGAGCACACGTCTG)

PIK3CA exon 20:
PIK3CA_20-seq1-UMI-P5-RC (CATTCCAGAGCCAAGCATCATNNNN

NNNNNNNAGATCGGAAGAGCGTCGTGTAG)

PIK3CA_20-seq2-UMI-P7-RC (AACAGCATGCATTGAACTGAAANN

NNNNNNNNAGATCGGAAGAGCACACGTCTG)

TP53 exon 6:
TP53_6-seq1-UMI-P5-RC (TGGGCAACCAGCCCTGTCGTCTNNNNN

NNNNNAGATCGGAAGAGCGTCGTGTAG)

TP53_6-seq2-UMI-P7-RC (GAGGAGGGGTTAAGGGTGGTTGNNNNN

NNNNNAGATCGGAAGAGCACACGTCTG)
```

PCR reactions were also performed to generate the target sequences for the DAPs. The following primers were used:

```
KRAS exon 2:
KRASex2 Fwd (AAGGCCTGCTGAAAATGACTGA)

KRASex2 Rev (CAAAGAATGGTCCTGCACCAGT)

PIK3CA exon 20:
PIK3CAex20 Fwd (ATGATGCTTGGCTCTGGAATG)

PIK3CAex20 Rev (TTTCAGTTCAATGCATGCTGTT)

TP53 exon 6:
TP53ex6 Fwd (AGACGACAGGGCTGGTTGCCCA)

TP53ex6 Rev (CAACCACCCTTAACCCCTCCTC)
```

All DAPs and target genes were gel purified using the Zymoclean Gel DNA Recovery Kits (Zymo Research).

Recombination-based dual adapter attachment—All reactions were conducted using either the NEBuilder HiFi DNA Assembly Master Mix (New England Biolabs), which contains an exonuclease, DNA Ligase and DNA polymerase. A ratio of 15:1 (DAP:target) was found yield the highest number of bacteria transformants, so this ratio was used for all subsequent studies. All 3 DAPs were pooled at equal amounts to generate a probe pool. Likewise, all PCR targets were pooled at equal amounts to generate a target pool. Reactions were set up as follows: 25 ul NEB HiFi DNA Assembly Master Mix, 5 ul DAP pool (30 ng/ul), 5 ul PCR target pool (2 ng/ul), 15 ul H2O and incubated at 50° C. for 30 min. Reactions were purified using 0.5×KAPA Pure Beads (from Roche) and eluted in 35 ul H$_2$O. Next, unreacted linear DNA was removed by adding 5 ul NEB Buffer 4, 5 ul ATP, 2 ul RecBCD (New England Biolabs) and 3 ul H₂O and incubating at 37° C. for 60 min and 70° C. for 30 min. The reaction was purified using 1.0×KAPA Pure Beads and eluted in 20 ul elution buffer. Finally, captured targets were PCR amplified using primers that target the NGS adapter sequences P5 and P7 (P5-PCR-universal: AAT GAT ACG GCG ACC ACC GAG ATC TAC ACT CTT TCC CTA CAC GAC GCT CTT CCG ATC T and P7-PCR-index CCGTTA: CAA GCA GAA GAC GGC ATA CGA GAT TAA CGG GTG ACT GGA GTT CAG ACG TGT GCT CTT CCG ATC T) in the DAP backbone using 22 cycles and a Tm of 60° C. PCR products were purified with 1.0×KAPA Pure Beads, eluted in 40 ul elution buffer and analyzed on an Agilent TapeStation D1000 assay.

Standard NGS library preparation—A standard ligation-based NGS library preparation was performed with custom adapters containing an 8 bp UMI located adjacent to the sample barcode. This library was created to directly compare ligation-based adapter attachment to recombination-based dual adapter attachment. The library was created using the KAPA Hyperprep kit (Roche) using custom adapters from IDT (AAT GAT ACG GCG ACC ACC GAG ATC TAC ACT CTT TCC CTA CAC GAC GCT CTT CCG ATC*T and /5 Phos/GA TCG GAA GAG CAC ACG TCT GAA CTC CAG TCA CGG AAC TNN NNN NNN ATC TCG TAT GCC GTC TTC TGC TTG). First, 5 ng of pooled PCR products were diluted in 50 ul 1×KAPA Frag Buffer. Next, 7 ul End Repair & A-Tailing Buffer and 3 ul End Repair & A-Tailing Enzyme Mix were added and the reaction was incubated at 65° C. for 30 min. Next, 5 ul of 1.5 uM custom adapter stock, 5 ul H₂O, 30 ul KAPA Ligation Buffer and DNA Ligase was added and incubated at 20° C. for 1 hr. Ligation reactions were purified by adding 88 ul KAPA Pure Beads and eluting in 25 ul elution buffer. Next, 20 ul of the purified ligation reaction was added to 25 ul KAPA HiFi HotStart ReadyMix (2×) and 5 ul Library Amplification Primer Mix (10×) and PCR amplified 22 cycles with a Tm of 60° C. The final PCR was purified with 1.0×KAPA Pure Beads, eluted in 40 ul elution buffer and analyzed on an Agilent TapeStation D1000 assay.

Sequencing Results—The DAP and KAPA libraries were multiplexed at 10 nM and run on an Illumina MiSeq using a micro flowcell with 2×150 bp sequencing. For each sample, reads were first sorted based on alignment to the three reference sequences. Next, unique 8 bp UMIs within each group were identified (Note: for DAP samples, the first 8 bp from the UMI1 sequence were used. The KAPA sample contained an 8 bp UMI adjacent to the sample barcode). In order for a UMI to be used in error correction, the UMI must be observed multiple times as low frequency variants in the UMI sequences may be errors. We used a cut-off of 5× to filter out UMIs and determined the percentage of UMIs over 5× out of the total number of UMIs per PCR target. Table 1 shows the recombination-based DAP method had significantly more UMIs above 5× than the traditional ligation-based method, suggesting recombination-based adapter attachment using DAPs is significantly more efficient than traditional ligation-based methods. This is significant as NGS library conversion is a critical step when analyzing circulating tumor DNA (ctDNA) for rare variant detection as inefficient adapter ligation can result in population sampling bias. DAPs can readily be used with PCR-based hotspot panels used for solid tumor and ctDNA analysis. Some current state of the art hotspot panels include an adapter ligation step following PCR amplification. Substituting DAP technology in place of traditional adapter ligation will increase NGS library conversion and improve overall sample representation in the sequence data. Moreover, DAPs allow high efficiency UMI attachment, which may offer superior error detection without sacrificing library conversion efficiency.

TABLE 1

NGS Library Conversion Comparison

| Amplicon | Library Prep: | Unique UMIs >= 5x | Total UMIs | % Unique UMIs >= 5x/total UMIs | % Increase |
|---|---|---|---|---|---|
| Amplicon: KRAS | DAP | 54,828 | 65,081 | 84% | 27% |
| | KAPA | 39,298 | 64,334 | 61% | |
| Amplicon: PIK3CA | DAP | 27,334 | 61,941 | 44% | 65% |
| | KAPA | 7,862 | 53,972 | 15% | |
| Amplicon: TP53 | DAP | 40,024 | 63,880 | 63% | 63% |
| | KAPA | 13,368 | 57,883 | 23% | |

Example 2

Comparison of TOPO T/A mediated ligation with the vector pCR4-TOPO and standard T/A ligation with NGS adapters from KAPA/Roche Preliminary NGS data has been generated comparing TOPO T/A mediated ligation with the vector pCR4-TOPO and standard T/A ligation with NGS adapters from KAPA/Roche. To measure capture efficiency, mutagenic libraries were made with 3 amplicons and then pooled. Capture efficiency was determine by counting the number of unique sequences and dividing by the total number of sequences. Wild-type amplicons were cloned and Sanger sequenced verified. Two different sets of primers were used in the mutagenic PCR (mPCR) reactions: 1) standard gene specific primers (see example 1) and 2) gene specific primers containing identical sequence plus partial NGS adapter sequences.

```
KRAS exon 2:
KRAS_2-seq1-UMI-P5-RC (TCAGTCATTTTCAGCAGGCCTTAGATC

GGAAGAGCGTCGTGTAG)

KRAS_2-seq2-UMI-P7-RC (ACTGGTGCAGGACCATTCTTTGAGATC

GGAAGAGCACACGTCTG)

PIK3CA exon 20:
PIK3CA_20-seq1-UMI-P5-RC (CATTCCAGAGCCAAGCATCATAGA

TCGGAAGAGCGTCGTGTAG)

PIK3CA_20-seq2-UMI-P7-RC (AACAGCATGCATTGAACTGAAAAG

ATCGGAAGAGCACACGTCTG)

TP53 exon 6:
TP53_6-seq1-UMI-P5-RC (TGGGCAACCAGCCCTGTCGTCTAGATC

GGAAGAGCGTC GTGTAG)

TP53_6-seq2-UMI-P7-RC (GAGGAGGGGTTAAGGGTGGTTGAGATC

GGAAGAGCACACGTCTG)
```

Both mPCR reactions used the same wild type clones as template. The mPCR products generated with standard primers were used as input for the KAPA Hyperprep Kit for Illumina sequencing, which consists of end repair/A-tailing, adapter ligation and PCR with Illumina NGS primers. The mPCR products generated with the second primer set were TOPO cloned into the pCR4-TOPO vector. Unreacted PCR products and TOPO vector were removed with Exonuclease V/RecBCD. Following purification, a final NGS library was created by PCR amplification with standard Illumina NGS primers. Both libraries sequenced as expected, demonstrating the TOPO cloned mPCR products are compatible with NGS sequencing. The TOPO library did not generate as many clusters/reads as the KAPA library, but it is not uncommon for libraries generated by different methods to cluster at different efficiencies. To measure the efficiency of the TOPO mediated ligation, we identified all unique mPCR products (as compared to their wild type sequence) using an Levenshtein/Edit Distance algorithm. Next, we treated each unique mPCR molecule as a barcode and counted total unique reads/barcodes present at 10× or higher. As a percentage of total reads, we found the TOPO vector captured more unique reads/barcodes for ⅔ of the amplicons. This result indicates that TOPO vector ligation efficiency is comparable or better when compared to the standard-Y-shaped adapter-ligation reactions used in standard NGS library preparation.

TABLE 1

NGS Library Conversion Comparison

| Amplicon | Library Prep: TOPO or KAPA | Unique Reads | Total Reads Mapped to Reference | % Unique Reads |
|---|---|---|---|---|
| Amplicon: KRAS | TOPO | 742 | 214,116 | 0.35 |
|  | KAPA | 987 | 429,960 | 0.23 |
| Amplicon: PIK3CA | TOPO | 785 | 186,850 | 0.42 |
|  | KAPA | 1098 | 559,500 | 0.20 |
| Amplicon: TP53 | TOPO | 1503 | 548,305 | 0.27 |
|  | KAPA | 2590 | 937,679 | 0.28 |

Example 3

TOPO-DAT and Recombinase-Mediated Target Enrichment

To demonstrate proof of principle for recombinase-mediated target enrichment with a closed circular dsDNA NGS library, a topoisomerase charged vector was used to topo clone an NGS library generated using a KAPA kit. Results were compared with the traditional target enrichment capture using same NGS libraries. Target enrichment was performed using xGen Hybridization probes from IDT. The probes were designed to capture the 773 bp UPP promoter.

```
>UPP-promoter
GGGTGAAAGCCAACCATCTTTGTTTCGGGGAACCGTGCTCGCCCCGTAAA

GTTAATTTTTTTTCCCGCGCAGCTTTAATCTTTCGGCAGAGAAGGCGTT

TTCATCGTAGCGTGGGAACAGAATAATCAGTTCATGTGCTATACAGGCAC

ATGGCAGCAGTCACTATTTTGCTTTTTAACCTTAAAGTCGTTCATCAATC

ATTAACTGACCAATCAGATTTTTTGCATTTGCCACTTATCTAAAAATACT

TTTGTATCTCGCAGATACGTTCAGTGGTTTCCAGGACAACACCCAAAAAA

AGGTATCAATGCCACTAGGCAGTCGGTTTTATTTTTGGTCACCCACGCAA

AGAAGCACCCACCTCTTTTAGGTTTTAAGTTGTGGGAACAGTAACACCGC

CTAGAGCTTCAGGAAAAACCAGTACCTGTGACCGCAATTCACCATGATGC

AGAATGTTAATTTAAACGAGTGCCAAATCAAGATTTCAACAGACAAATCA

ATCGATCCATAGTTACCCATTCCAGCCTTTTCGTCGTCGAGCCTGCTTCA

TTCCTGCCTCAGGTGCATAACTTTGCATGAAAAGTCCAGATTAGGGCAGA

TTTTGAGTTTAAAATAGGAAATATAAACAAATATACCGCGAAAAAGGTTT

GTTTATAGCTTTTCGCCTGGTGCCGTACGGTATAAATACATACTCTCCTC

CCCCCCCTGGTTCTCTTTTTCTTTTGTTACTTACATTTTACCGTTCCGTC

ACTCGCTTCACTCAACAACAAAA
```

NGS libraries were made with genomic DNA from 4 *Pichia Pastoris* strains using the KAPA kit (as described in the previous example). For the traditional bait capture, each final NGS library was quantified using the Qubit broad range dsDNA assay and 125 ng of each library was combined for a total of 500 ng and combined with 2.5 ul salmon sperm DNA (10 mg/ml). The mixture was purified using 1.8×Kapa Beads and eluted in 9.5 ul xGen 2× Hybridization Buffer, 3 ul xGen Hybridization Buffer Enhancer, 2 ul Blocking Oligos and 4.5 ul xGen Lockdown Probes targeting the UPP promoter. The reaction was heated at 95° C. for 30 sec and 65° C. for 16 hrs. The hybridization reaction was bound to streptavidin beads and washed according to the IDT xGen hybridization capture of DNA libraries protocol. Following washing, 16 cycles of post-capture PCR were performed. PCR products were purified with 1.5×KAPA Pure Beads, eluted in 26 ul elution buffer and analyzed on an Agilent TapeStation D1000 assay.

For the RecA-mediated capture, the purified post-ligation reaction was PCR amplified using 30 cycles and a Tm of 60. The PCR reaction was diluted 1/10 and 4 ul were mixed with 1 ul pCR4-TOPO and 1 ul salt solution, and incubated at room temperature for 30 mins. Reactions were transformed into NEB 10-beta electrocompetent cells and plated over 30 LB/Amp plates to generate approximately 1.5 M colonies. All plates were scraped, cells combined, resuspended in LB/Amp media and 9 ml used to isolate supercoiled plasmids using the Monarch Plasmid Prep kit (New England Biolabs). The *Pichia Pastoris* genome is approximately 9.4 Mb, so 1.5 M clones with 200-300 bp fragments=300-450 Mb total genome representation (30-45× coverage).

Nucleofilaments were formed by combining 1 ul (2 ug) of RecA protein (New England Biolabs), 3 ul 10× RecA Buffer (New England Biolabs), 7 ul xGen Lockdown Probes targeting the UPP promoter, 6 ul 2 mM ATP-γ-S, 2 ul ATP (10 mM) and 6 ul of $H_2O$, and incubating at 37° C. for 15 min. Next, 5 ul supercoiled NGS plasmid library (100 ng/ul) was added (500 ng total) and incubated at 37° C. for 20 min. The reaction was terminated by adding 0.5 ul Proteinase K (20 mg/ml) and 1 ul 5% SDS and incubating at 37° C. for 10 min. Finally, 1 ul 100 mM PMSF was added to stop Proteinase K activity.

The hybridization reaction was bound to streptavidin beads by incubation at room temperature for 40 min and washed twice with 100 ul 1× Bind & Washing (B&W) buffer (5 mM Tris-HCl, pH7.5, 0.5 mM EDTA and 1 M NaCl) and once with 100 ul H2O. The beads were resuspended in 20 ul $H_2O$ and combined 25 ul KAPA HiFi HotStart ReadyMix (2×) and 5 ul Library Amplification Primer Mix (10×) and PCR amplified 22 cycles with a Tm of 60° C. The final PCR was purified with 1.0×KAPA Pure Beads, eluted in 40 ul elution buffer and analyzed on an Agilent TapeStation D1000 assay.

Figure 9:
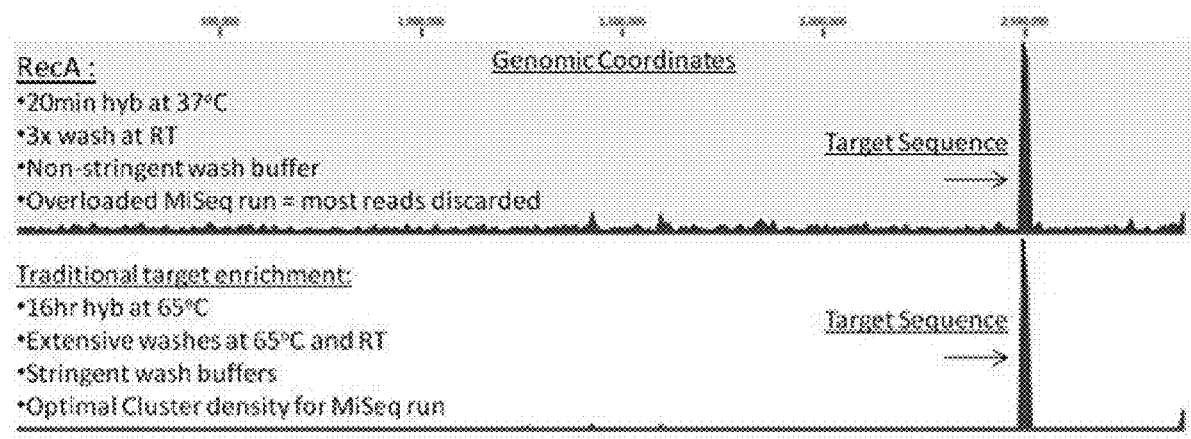
FIG. 9 shows a schematic of a comparison between RecA-mediated capture with Dual Adapter technology and traditional probe-based target enrichment using NGS libraries created with standard Y-shaped adapters with the same sample DNA. The RecA hybridization protocol consists of a 20 minute hybridization at 37° C. and three washes at room temperature with non-stringent buffer. Traditional target enrichment consists of a 16 hour hybridization at 65° C. and five washes at 65° C. and room temperature with stringent wash buffers. Both samples were run on an Illumina Miseq (2×150 bp) on 2 different dates. The traditional target enrichment sample generated optimal cluster density and high quality sequence reads. The RecA capture run was overloaded with an excessive cluster density, which resulting in very few high quality sequence reads. Nevertheless, the data from RecA capture shows enrichment of the target DNA sequence with only a fraction of the data (Note: the Y-axis scale is much lower for the RecA data and the off-target sequence is more apparent due to the limited amount of sequence data).

Sequencing Results—Both captures were sequenced separately on an Illumina Miseq (2×150 bp). FIG. 9 shows the RecA mediated capture generated a similar genome profile as the control with reads stacking at the target gene genomic coordinates. The sequencing run with the RecA samples was overloaded, so most reads were discarded due to quality issues. As a result, the peak height is not as high as the control sample and more background peaks are apparent. This was the first attempt at the new protocol, but we were able to demonstrate proof of principle with less than optimal data.

Prior reports suggests the true value of this method is the ability to capture small target areas with minimal off-target, which is difficult to achieve with traditional bait capture. However, the real value of the invention is the ability to perform target enrichment rapidly at low temperature, which should reduce sample oxidation and reduce artifacts when analyzing specimens for rare variants. Moreover, combining recombinase-mediated target enrichment with dual adapter technology solves multiple issues associated with rare variant detection. Topoisomerase charged dual adapter technology facilitates high efficiency UMI attachment to sample nucleic acid, which is required for error correction, and the resulting circular dsDNA molecules allow recombinase-mediated target enrichment without stability probes. The previous example used a plasmid and relied on *E. coli* transformation for super coiling the plasmid DNA, however, non-plasmid dual adapter molecules may be supercoiled in vitro using DNA Gyrase or ethidium bromide. Also, closed circular dsDNA dual adapter probes may not need to be supercoiled to form stable D-loops as stable D-loops have be shown to be formed with relaxed plasmid DNA (ref) and the strand invasion process by the nucleofilament itself may introduce enough negative supercoiling to stabilize the structure for target enrichment.

REFERENCES

1. Kamps R, Brandão R D, Bosch B J, et al. Next-Generation Sequencing in Oncology: Genetic Diagnosis, Risk Prediction and Cancer Classification. Int J Mol Sci. 2017; 18(2):308. Published 2017 Jan. 31. doi:10.3390/ijms18020308
2. Gray P. N.; Dunlop, C.; Elliott, A. Not All Next Generation Sequencing Diagnostics are Created Equal: Understanding the Nuances of Solid Tumor Assay Design for Somatic Mutation Detection. Cancers 2015, 7, 1313-1332
3. Shu, Y., Wu, X., Tong, X. et al. Circulating Tumor DNA Mutation Profiling by Targeted Next Generation Sequencing Provides Guidance for Personalized Treatments in Multiple Cancer Types. Sci Rep 7, 583 (2017). doi.org/10.1038/s41598-017-00520-1
4. Fiala, C., Diamandis, E. P. Utility of circulating tumor DNA in cancer diagnostics with emphasis on early detection. BMC Med 16, 166 (2018). doi.org/10.1186/s12916-018-1157-9
5. Hahn, S.; Garvin, A. M.; Di Naro, E.; Holzgreve, W. Allele drop-out can occur in alleles differing by a single nucleotide and is not alleviated by preamplification or minor template increments. Genet. Test 1998, 2, 351-355.
6. Barnard, R.; Futo, V.; Pecheniuk, N.; Slattery, M.; Walsh, T. Pcr bias toward the wild-type k-ras and p53 sequences: Implications for pcr detection of mutations and cancer diagnosis. BioTechniques 1998, 25, 684-691.
7. Hodges, E.; Xuan, Z.; Balija, V.; Kramer, M.; Molla, M. N.; Smith, S. W.; Middle, C. M.; Rodesch, M. J.; Albert, T. J.; Hannon, G. J.; et al. Genome-wide in situ exon capture for selective resequencing. Nat. Genet. 2007, 39, 1522-1527.
8. Okou, D. T.; Steinberg, K. M.; Middle, C.; Cutler, D. J.; Albert, T. J.; Zwick, M. E. Microarray-based genomic selection for high-throughput resequencing. Nat. Methods 2007, 4, 907-909.
9. Albert, T. J.; Molla, M. N.; Muzny, D. M.; Nazareth, L.; Wheeler, D.; Song, X.; Richmond, T. A.; Middle, C. M.; Rodesch, M. J.; Packard, C. J.; et al. Direct selection of human genomic loci by microarray hybridization. Nat. Methods 2007, 4, 903-905.
10. Mamanova, L.; Coffey, A. J.; Scott, C. E.; Kozarewa, I.; Turner, E. H.; Kumar, A.; Howard, E.; Shendure, J.; Turner, D. J. Target-enrichment strategies for next-generation sequencing. Nat. Methods 2010, 7, 111-118.
11. Pritchard, C. C.; Salipante, S. J.; Koehler, K.; Smith, C.; Scroggins, S.; Wood, B.; Wu, D.; Lee, M. K.; Dintzis, S.; Adey, A.; et al. Validation and implementation of targeted capture and sequencing for the detection of actionable mutation, copy number variation, and gene rearrangement in clinical cancer specimens. J. Mol. Diagn. 2014, 16, 56-67.
12. Frampton, G. M.; Fichtenholtz, A.; Otto, G. A.; Wang, K.; Downing, S. R.; He, J.; Schnall-Levin, M.; White, J.; Sanford, E. M.; An, P.; et al. Development and validation of a clinical cancer genomic profiling test based on massively parallel DNA sequencing. Nat. Biotechnol. 2013, 31, 1023-1031.
13. Wagle, N.; Berger, M. F.; Davis, M. J.; Blumenstiel, B.; Defelice, M.; Pochanard, P.; Ducar, M.; van Hummelen, P.; Macconaill, L. E.; Hahn, W. C.; et al. High-throughput detection of actionable genomic alterations in clinical tumor samples by targeted, massively parallel sequencing. Cancer Discov. 2011, 2, 82-93.
14. Lanman R B, Mortimer S A, Zill O A, Sebisanovic D, Lopez R, Blau S, et al. (2015) Analytical and Clinical Validation of a Digital Sequencing Panel for Quantitative, Highly Accurate Evaluation of Cell-Free Circulating Tumor DNA. PLoS ONE 10(10): e0140712.
15. Schmitt M W, et al. Detection of ultra-rare mutations by next-generation sequencing. Proc Natl Acad Sci USA. 2012; 109:14508-14513.
16. Fox, E., Reid-Bayliss, K.; Emond, M.; Loeb, L. Next Gener Seq Appl. Accuracy of Next Generation Sequencing Platforms 2014; 1: 1000106.
17. Newman, A, et al. Integrated digital error suppression for improved detection of circulating tumor DNA Nat Biotechnol. 2016 May; 34(5): 547-555.
18. Costello, M, et al. Discovery and characterization of artifactual mutations in deep coverage targeted capture sequencing data due to oxidative DNA damage during sample preparation. Nucleic Acid Research. 2013; 41(6): e67-e67
19. Honigberg S M, Rao B J and Radding C M. Ability of RecA protein to promote a search for rare sequences in duplex DNA. Proc. Nati. Acad. Sci. USA Vol. 83, pp. 9586-9590, December 1986
20. Bakhyt Zhumabayeva, Alex Chenchik, and Paul D. Siebert. RecA-Mediated Affinity Capture: A Method for Full-Length cDNA Cloning. BioTechniques 1999 27:4, 834-845
21. Holger Welder, Hilden and Erika Wedler, Hilden. RECOMBINASE MEDIATED TARGETED DNA ENRICHMENT FOR NEXT GENERATION SEQUENCING. US 2015/0197787 A1 United States Patent and Trademark Office, 16 Jul. 2015.

22. Shuman S. Recombination mediated by vaccinia virus DNA topoisomerase I in *Escherichia coli* is sequence specific. Proc Natl Acad Sci USA. 1991 Nov. 15; 88(22): 10104-8.
23. Shuman S. Novel approach to molecular cloning and polynucleotide synthesis using vaccinia DNA topoisomerase. J Biol Chem. 1994 Dec. 23; 269(51):32678-84.
24. Jonathan D. Chesnut, Stewart Shuman, Knut R. Madden, John A. Heyman, Robert P. Bennett. METHODS AND REAGENTS FOR MOLECULAR CLONING. US 2003/0022179 A1 United States Patent and Trademark Office, 30 Jan. 2003
25. Gibson, D. G. et. al. Enzymatic assembly of DNA molecules up to several hundred kilobases. Nature Methods. 2009 May; 6(5):343-5.
26. Gibson, D. G. et al. Chemical synthesis of the mouse mitochondrial genome. Nature Methods. 2010 November; 7(11):901-3.
27. Zhang, Y.; Werling, U.; Edelmann, W. Seamless Ligation Cloning Extract (SLiCE) Cloning Method Methods Mol Biol. 2014; 1116: 235-244.
28. Li, M.; Elledge S. SLIC: a method for sequence- and ligation-independent cloning. Methods Mol Biol. 2012; 852:51-9.
29. Jon Ness and Jeremy S. Minshull. METHODS, COMPOSITIONS, AND KITS FOR ONE-STEP DNA CLONING USING DNA TOPOISOMERASE WO 2009/017673 A2 World Intellectual Property Organization International Bureau 5 Feb. 2009
30. P Hsieh, C S Camerini-Otero, R D Camerini-Otero. The synapsis event in the homologous pairing of DNAs: RecA recognizes and pairs less than one helical repeat of DNA. Proceedings of the National Academy of Sciences July 1992, 89 (14) 6492-6496.
31. Stephen C. Kowalczykowski and Angela K. Eggleston. HOMOLOGOUS PAIRING AND DNA STRAND-EXCHANGE PROTEINS. Annual Review of Biochemistry 1994 63:1, 991-1043
32. B J Rao, M Dutreix, C M Radding. Stable three-stranded DNA made by RecA protein. Proceedings of the National Academy of Sciences April 1991, 88 (8) 2984-2988
33. Tracy R B, Kowalczykowski S C In vitro selection of preferred DNA pairing sequences by the *Escherichia coli* RecA protein. Dev. 1996 Aug. 1; 10(15):1890-903.
34. S C Kowalezykowski. Biochemistry of Genetic Recombination: Energetics and Mechanism of DNA Strand Exchange. Annual Review of Biophysics and Biophysical Chemistry 1991 20:1, 539-575
35. Radding C M. J Biol Chem. 1991 Mar. 25; 266(9):5355-8. Helical interactions in homologous pairing and strand exchange driven by RecA protein.
36. Honigberg S M, Rao B J, Radding C M. Ability of RecA protein to promote a search for rare sequences in duplex DNA. Proc Natl Acad Sci USA. 1986 December; 83(24): 9586-90.
37. Kirkpatrick D P, Radding C M. RecA protein promotes rapid RNA-DNA hybridization in heterogeneous RNA mixtures. Nucleic Acids Res. 1992; 20(16):4347-4353. doi:10.1093/nar/20.16.4347.
38. Assembly of RecA-like recombinases: Distinct roles for mediator proteins in mitosis and meiosis. Stephen L. Gasior, Heidi Olivares, Uy Ear, Danielle M. Hari, Ralph Weichselbaum, Douglas K. Bishop. Proceedings of the National Academy of Sciences July 2001, 98 (15) 8411-8418
39. Shibata T, Osber L, Radding C M. Purification of recA protein from *Escherichia coli*. Methods Enzymol. 1983; 100:197-209.
40. Madiraju M V, Templin A, Clark A J. Properties of a mutant recA-encoded protein reveal a possible role for *Escherichia coli* recF-encoded protein in genetic recombination. Proc Natl Acad Sci USA. 1988; 85(18):6592-6596. doi:10.1073/pnas.85.18.6592
41. Kawashima, H., Horii, T., Ogawa, T. et al. Functional domains of *Escherichia coli* recA protein deduced from the mutational sites in the gene. Molec Gen Genet 193, 288-292 (1984).
42. Yonesaki T, Minagawa T. T4 phage gene uvsX product catalyzes homologous DNA pairing. EMBO J. 1985 Dec. 1; 4(12):3321-7.
43. Lovett C M Jr, Roberts J W. Purification of a RecA protein analogue from *Bacillus subtilis*. J Biol Chem. 1985 Mar. 25; 260(6):3305-13.
44. Kmiec E, Holloman W K. Homologous pairing of DNA molecules promoted by a protein from *Ustilago*. Cell. 1982 June; 29(2):367-74.
45. Angov E, Camerini-Otero R D. The recA gene from the thermophile *Thermus aquaticus* YT-1: cloning, expression, and characterization. J Bacteriol. 1994; 176(5): 1405-1412. doi:10.1128/jb.176.5.1405-1412.1994
46. Kato, R. and Kuramitsu, S. (1999), Characterization of thermostable RecA protein and analysis of its interaction with single-stranded DNA. European Journal of Biochemistry, 259: 592-601.
47. Shinohara, A., Ogawa, H., Matsuda, Y. et al. Cloning of human, mouse and fission yeast recombination genes homologous to RAD51 and recA. Nat Genet 4, 239-243
48. Potapov V, Ong J L (2017) Examining Sources of Error in PCR by Single-Molecule Sequencing. PLoS ONE 12(1): e0169774.
49. Chong H K, Wang T, Lu H M, Seidler S, Lu H, Keiles S, et al. (2014) The Validation and Clinical Implementation of BRCAplus: A Comprehensive High-Risk Breast Cancer Diagnostic Assay. PLoS ONE 9(5): e97408.
50. Tate, J G. et. al. COSMIC: the Catalogue Of Somatic Mutations In Cancer, Nucleic Acids Research, Volume 47, Issue D1, 8 Jan. 2019, Pages D941-D947.
51. Hong, Y. et al. Antitumor Activity of BRAF Inhibitor Vemurafenib in Preclinical Models of BRAF-Mutant Colorectal Cancer. Cancer Res Feb. 1, 2012 (72) (3) 779-789; DOI: 10.1158/0008-5472.CAN-11-2941.
52. Khozin S, Blumenthal G M, Jiang X, et al. U. S. Food and Drug Administration approval summary: Erlotinib for the first-line treatment of metastatic non-small cell lung cancer with epidermal growth factor receptor exon 19 deletions or exon 21 (L858R) substitution mutations. Oncologist. 2014; 19(7):774-779.
53. Chan, T. A. et al. Development of tumor mutation burden as an immunotherapy biomarker: utility for the oncology clinic. Annals of Oncology, Volume 30, Issue 1, 44-56.
54. Westdorp, H., Fennemann, F. L., Weren, R. D. A. et al. Opportunities for immunotherapy in microsatellite instable colorectal cancer. Cancer Immunol Immunother 65, 1249-1259 (2016).
55. Bacher, Jeffery W., et al. "Development of a fluorescent multiplex assay for detection of MSI-High tumors." Disease markers 20.4, 5 (2004): 237-250.
56. Treangen T J, Salzberg S L. Repetitive DNA and next-generation sequencing: computational challenges and solutions [published correction appears in Nat Rev Genet. 2012 February; 13(2):146]. Nat Rev Genet. 2011; 13(1):36-46.

57. Kohlmann, W., and S. B. Gruber. "GeneReviews®." (1993).
58. Havel, J. J., Chowell, D. & Chan, T. A. The evolving landscape of biomarkers for checkpoint inhibitor immunotherapy. Nat Rev Cancer 19, 133-150 (2019).
59. Abkevich, V., et al. "Patterns of genomic loss of heterozygosity predict homologous recombination repair defects in epithelial ovarian cancer." British journal of cancer 107.10 (2012): 1776-1782.
60. Kohn, Elise C., Jung-min Lee, and S. Percy Ivy. "The HRD decision-which PARP inhibitor to use for whom and when." Clinical Cancer Research 23.23 (2017): 7155-7157.
61. Patel S J, Sanjana N E, Kishton R J, et al. Identification of essential genes for cancer immunotherapy. Nature. 2017; 548(7669):537-542. doi:10.1038/nature23477.
62. Giornelli G H. Management of relapsed ovarian cancer: a review. Springerplus. 2016; 5(1):1197. Published 2016 Jul. 28. doi:10.1186/s40064-016-2660-0.
63. Rahner N, Steinke V. Hereditary cancer syndromes. Dtsch Arztebl Int. 2008; 105(41):706-714. doi:10.3238/arztebl.2008.0706.
64. Rosati, E., Dowds, C. M., Liaskou, E. et al. Overview of methodologies for T-cell receptor repertoire analysis. BMC Biotechnol 17, 61 (2017).
65. Chaudhary N, Wesemann D R. Analyzing Immunoglobulin Repertoires. Front Immunol. 2018; 9:462. Published 2018 Mar. 14. doi:10.3389/fimmu.2018.00462
66. Levine, Bruce L., et al. "Global manufacturing of CAR T cell therapy." Molecular Therapy-Methods & Clinical Development 4 (2017): 92-101.
67. Nachmanson D, Lian S, Schmidt E K, et al. Targeted genome fragmentation with CRISPR/Cas9 enables fast and efficient enrichment of small genomic regions and ultra-accurate sequencing with low DNA input (CRISPR-D S). Genome Res. 2018; 28(10):1589-1599. doi:10.1101/gr.235291.118.
68. Lee J, Lim H, Jang H, et al. CRISPR-Cap: multiplexed double-stranded DNA enrichment based on the CRISPR system. Nucleic Acids Res. 2019; 47(1):e1. doi:10.1093/nar/gky820
69. Fu, Y., Wu, P., Beane, T. et al. Elimination of PCR duplicates in RNA-seq and small RNA-seq using unique molecular identifiers. BMC Genomics 19, 531 (2018).
70. Carethers, John M., and Stephanie S. Tseng-Rogenski. "EMAST is a form of microsatellite instability that is initiated by inflammation and modulates colorectal cancer progression." Genes 6.2 (2015): 185-205.
71. Coupland P, Chandra T, Quail M, Reik W, Swerdlow H. Direct sequencing of small genomes on the Pacific Biosciences R S without library preparation. Biotechniques. 2012; 53(6):365-372. doi:10.2144/000113962
72. van Dijk, Erwin L., et al. "The third revolution in sequencing technology." Trends in Genetics 34.9 (2018): 666-681.
73. Talerico M, Berget S M. Effect of 5' splice site mutations on splicing of the preceding intron. Mol Cell Biol. 1990; 10(12):6299-6305. doi:10.1128/mcb.10.12.6299.
74. Knight, Simon Robert, Adam Thorne, and Maria Letizia Lo Faro. "Donor-specific cell-free DNA as a biomarker in solid organ transplantation. A systematic review." Transplantation 103.2 (2019): 273-283.
75. Mertens, Fredrik, et al. "The emerging complexity of gene fusions in cancer." Nature Reviews Cancer 15.6 (2015): 371-381.
76. Maher, Christopher A., et al. "Transcriptome sequencing to detect gene fusions in cancer." Nature 458.7234 (2009): 97-101.
77. Holmes, Allyson, et al. "Mechanistic signatures of HPV insertions in cervical carcinomas." NPJ genomic medicine 1.1 (2016): 1-16.
78. Shembekar, Nachiket, et al. "Droplet-based microfluidics in drug discovery, transcriptomics and high-throughput molecular genetics." Lab on a Chip 16.8 (2016): 1314-1331.
79. Allyse, Megan, et al. "Non-invasive prenatal testing: a review of international implementation and challenges." International journal of women's health 7 (2015): 113.

What is claimed is:

1. A linear double-stranded DNA (dsDNA) Dual Adapter molecule configured to capture or select a specific nucleic acid sequence for targeted sequencing, the Dual Adapter molecule comprising:
- a first homology region (HR1) that comprises a first target homology sequence ranging from a length of 10 nucleotides to 1000 nucleotides that is substantially homologous to a region located 5' to a predetermined region within a first target DNA, cDNA, and/or RNA molecule, wherein HR1 is comprised of a single stranded 5' or 3' protruding end;
- a second homology region (HR2) that comprises a second target homology sequence ranging from a length of 10 nucleotides to 1000 nucleotides that is substantially homologous to a region located 3' to a predetermined region within the first target DNA, cDNA, and/or RNA molecule, wherein HR2 is comprised of a single stranded 5' or 3' protruding end and the first and second homology regions function as a pair (HR1:HR2) and comprise different nucleotide sequences that bind or hybridize to different regions of the same target nucleic acid molecule to form a hybridization complex consisting of the Dual Adapter molecule and target nucleic acid molecule that may be isolated or separated from non-targeted nucleic acids;
- a first unique molecular identifier (UMI1) disposed directly adjacent to HR1 that comprises a random nucleic acid sequence of at least 2 nucleotides;
- a second unique molecular identifier (UMI2) disposed directly adjacent to HR2 that comprises a random nucleic acid sequence of at least 2 nucleotides;
- a first Adapter sequence (AS1) disposed directly adjacent to UMI1;
- a second Adapter sequence (AS2) disposed directly adjacent to UMI2, wherein the first and second Adapter sequences comprise different nucleotide sequences and bind different primers;
- optionally a first tandem restriction or nicking enzyme sequence positioned such that it forms a stem-loop or hairpin structure and can be cleaved or nicked by the corresponding enzyme when a single strand is generated by a DNA polymerase during isothermal amplification or rolling circle amplification and disposed 5' of, and optionally flanking AS1;
- optionally a second tandem restriction or nicking enzyme sequence positioned such that it forms a stem-loop or hairpin structure and can be cleaved or nicked by the corresponding enzyme when a single strand is generated by a DNA polymerase during isothermal amplification or rolling circle amplification and disposed 3' of, and optionally flanking AS2;
- optionally at least one or more of the following, (i) a gene encoding a selectable marker, optionally an antibiotic resistance marker, and (ii) an origin of replication.

2. A library comprising a plurality of different Dual Adapter molecule species of claim 1, wherein each Dual Adapter molecule species comprises a different nucleic acid, and wherein each Dual Adapter molecule species comprises an HR1:HR2 pair that comprises a first and second target homology sequences that differ from the first and second target homology sequences of the other HR1:HR2 pairs, wherein each unique HR1:HR2 pair of each Dual Adapter molecule species targets a different predetermined region within a population of DNA, cDNA, and/or RNA molecules and wherein each dual adapter molecule comprises unique random UMI1 and UMI2 sequences and UMI1-UMI2 pair.

3. A method that attaches unique molecular identifiers (UMIs) and adapter sequences, and selectively captures non-denatured double stranded nucleic acid sequences simultaneously using the library of Dual Adapter molecules species of claim 2, the method comprising:
- a. providing a reaction mixture comprising a nuclease activity and the library of dual adapter molecules of claim 2, and generating single stranded regions at the ends of the dual adapter molecules;
- b. optionally providing a reaction mixture comprising a nuclease activity and population of target nucleic acids (optionally DNA, cDNA and/or RNA molecules), and generating single stranded regions at the ends of the target nucleic acid molecules;
- c. providing a reaction mixture comprising a library of Dual Adapter molecules of claim 2 that comprise single-stranded HR1 and HR2 domains, a nucleic acid sample that comprises a population of target nucleic acids, optionally DNA, cDNA and/or RNA molecules, that optionally comprise single-stranded ends, a DNA polymerase activity, a nuclease activity and a DNA ligase activity, wherein the reaction mixture is incubated under conditions that facilitate hybridization between single-stranded complementary regions of the Dual Adapter molecules-HR1:HR2 sequences and target nucleic acids, to generate a covalently closed circular double stranded nucleic acid molecule comprising the Dual Adapter molecule and target sequence;
- d. optionally providing a reaction mixture comprising a library of Dual Adapter molecules of claim 2, a nuclease activity, a DNA polymerase activity, and a DNA ligase activity and a population of target nucleic acids, optionally DNA, cDNA, and/or RNA molecules, wherein the reaction mixture is incubated under conditions that generate single-stranded regions in the target nucleic acid molecules and Dual Adapter molecule HR1 and HR2 regions, wherein the reaction mixture is incubated under conditions that facilitate hybridization of single-stranded complementary regions between the Dual Adapter molecule HR1:HR2 sequences and target nucleic acids, to generate a covalently closed circular double stranded nucleic acid molecule comprising the Dual Adapter molecule and target sequence;

e. providing a reaction mixture comprising a covalently closed circular double stranded nucleic acid molecule comprising the Dual Adapter molecule and target sequence, amplification primers, optionally PCR primers, adapted to hybridize to AS1 and AS2, and reagents to amplify the nucleic acid region bounded by AS1 and AS2 to produce amplification products, optionally adapted for next generation sequencing;

f. optionally providing a reaction mixture comprising a covalently closed circular double stranded nucleic acid molecule comprising the Dual Adapter molecule and target sequence, amplification primers, optionally a primers including a modified nucleotide comprising an affinity tag to facilitate separation, wherein optionally the affinity tag is a biotin molecule or a hapten, adapted to hybridize to AS1 and/or AS2 or other region on the molecule, and reagents to amplify the nucleic acid using rolling circle or isothermal amplification to produce DNA concatemers of repeating units comprising AS1/UMI1/target sequence/UMI2/AS2 that are optionally separated into individual units with a restriction or nicking enzyme or PCR amplified according to step e.

* * * * *

```
                       SEQUENCE LISTING

<160> NUMBER OF SEQ ID NOS: 28

<210> SEQ ID NO 1
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
agatcggaag agcgtcgtgt aggcttcctc gctcactgac tcgct              45

<210> SEQ ID NO 2
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agatcggaag agcacacgtc tgccgggagc tgcatgtgtc agagg              45
```

```
<210> SEQ ID NO 3
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(32)
<223> OTHER INFORMATION: a, c, t, g, unknown or other

<400> SEQUENCE: 3
tcagtcattt tcagcaggcc ttnnnnnnnn nnagatcgga agagcgtcgt gtag            54

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(32)
<223> OTHER INFORMATION: a, c, t, g, unknown or other

<400> SEQUENCE: 4
actggtgcag gaccattctt tgnnnnnnnn nnagatcgga agagcacacg tctg            54

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (22)..(31)
<223> OTHER INFORMATION: a, c, t, g, unknown or other

<400> SEQUENCE: 5
cattccagag ccaagcatca tnnnnnnnnn nagatcggaa gagcgtcgtg tag             53

<210> SEQ ID NO 6
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(32)
<223> OTHER INFORMATION: a, c, t, g, unknown or other

<400> SEQUENCE: 6
aacagcatgc attgaactga aannnnnnnn nnagatcgga agagcacacg tctg            54

<210> SEQ ID NO 7
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(32)
<223> OTHER INFORMATION: a, c, t, g, unknown or other
```

<400> SEQUENCE: 7
tgggcaacca gccctgtcgt ctnnnnnnnn nnagatcgga agagcgtcgt gtag       54

<210> SEQ ID NO 8
<211> LENGTH: 54
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (23)..(32)
<223> OTHER INFORMATION: a, c, t, g, unknown or other

<400> SEQUENCE: 8
gaggaggggt taagggtggt tgnnnnnnnn nnagatcgga agagcacacg tctg       54

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aaggcctgct gaaaatgact ga                                          22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caaagaatgg tcctgcacca gt                                          22

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgatgcttg gctctggaat g                                           21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttcagttca atgcatgctg tt                                          22

<210> SEQ ID NO 13
<211> LENGTH: 22
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 13
agacgacagg gctggttgcc ca                                              22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
caaccaccct taacccctcc tc                                              22

<210> SEQ ID NO 15
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aatgatacgg cgaccaccga gatctacact ctttccctac acgacgctct tccgatct      58

<210> SEQ ID NO 16
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
caagcagaag acggcatacg agattaacgg gtgactggag ttcagacgtg tgctcttccg    60
atct                                                                  64

<210> SEQ ID NO 17
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
aatgatacgg cgaccaccga gatctacact ctttccctac acgacgctct tccgatct      58

<210> SEQ ID NO 18
<211> LENGTH: 71
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (40)..(47)
<223> OTHER INFORMATION: a, c, t, g, unknown or other

<400> SEQUENCE: 18
gatcggaaga gcacacgtct gaactccagt cacggaactn nnnnnnnatc tcgtatgccg    60
```
tcttctgctt g                                                          71

<210> SEQ ID NO 19
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
tcagtcattt tcagcaggcc ttagatcgga agagcgtcgt gtag                      44

<210> SEQ ID NO 20
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
actggtgcag gaccattctt tgagatcgga agagcacacg tctg                      44

<210> SEQ ID NO 21
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cattccagag ccaagcatca tagatcggaa gagcgtcgtg tag                       43

<210> SEQ ID NO 22
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aacagcatgc attgaactga aaagatcgga agagcacacg tctg                      44

<210> SEQ ID NO 23
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tgggcaacca gccctgtcgt ctagatcgga agagcgtcgt gtag                      44

<210> SEQ ID NO 24
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gaggaggggt taagggtggt tgagatcgga agagcacacg tctg                      44

```
<210> SEQ ID NO 25
<211> LENGTH: 773
<212> TYPE: DNA
<213> ORGANISM: Unknown
<220> FEATURE:
<223> OTHER INFORMATION: Description of Unknown:
      UPP promoter sequence

<400> SEQUENCE: 25
gggtgaaagc caaccatctt tgtttcgggg aaccgtgctc gccccgtaaa gttaattttt    60
ttttcccgcg cagctttaat ctttcggcag agaaggcgtt ttcatcgtag cgtgggaaca   120
gaataatcag ttcatgtgct atacaggcac atggcagcag tcactatttt gcttttaac   180 cttaaagtcg ttcatcaatc attaactgac caatcagatt ttttgcattt gccacttatc   240
taaaaatact tttgtatctc gcagatacgt tcagtggttt ccaggacaac acccaaaaaa   300
aggtatcaat gccactaggc agtcggtttt atttttggtc acccacgcaa agaagcaccc   360
acctctttta ggtttaagt tgtgggaaca gtaacaccgc ctagagcttc aggaaaaacc    420
agtacctgtg accgcaattc accatgatgc agaatgttaa tttaaacgag tgccaaatca   480
agatttcaac agacaaatca atcgatccat agttacccat tccagccttt tcgtcgtcga   540
gcctgcttca ttcctgcctc aggtgcataa cttttgcatga aaagtccaga ttagggcaga   600
ttttgagttt aaaataggaa atataaacaa atataccgcg aaaaaggttt gtttatagct    660
tttcgcctgg tgccgtacgg tataaataca tactctcctc ccccccctgg ttctcttttt    720
cttttgttac ttcattttta ccgttccgtc actcgcttca ctcaacaaca aaa            773

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(17)
<223> OTHER INFORMATION: a, c, t, g, unknown or other

<400> SEQUENCE: 26
aagggnnnnn nnnnnnn                                                    17

<210> SEQ ID NO 27
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(12)
<223> OTHER INFORMATION: a, c, t, g, unknown or other

<400> SEQUENCE: 27
nnnnnnnnnn nnccctt                                                    17

<210> SEQ ID NO 28
<211> LENGTH: 16
<212> TYPE: DNA
<213> ORGANISM: Artificial Sequence
<220> FEATURE:
<223> OTHER INFORMATION: Description of Artificial Sequence: Synthetic
```

```
                           oligonucleotide
<220> FEATURE:
<221> NAME/KEY: modified_base
<222> LOCATION: (5)..(16)
<223> OTHER INFORMATION: a, c, t, g, unknown or other

<400> SEQUENCE: 28
agggnnnnnn nnnnnn                                                         16
```